United States Patent
Lu et al.

(10) Patent No.: US 10,640,831 B2
(45) Date of Patent: May 5, 2020

(54) BIOMARKERS FOR HEAD AND NECK CANCER AND METHODS OF THEIR USE

(71) Applicant: THE REGENTS OF THE UNIVERSITY OF COLORADO, A BODY CORPORATE, Denver, CO (US)

(72) Inventors: Shi-long Lu, Greenwood Village, CO (US); John Song, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 33 days.

(21) Appl. No.: 15/519,758

(22) PCT Filed: Oct. 16, 2015

(86) PCT No.: PCT/US2015/055958
§ 371 (c)(1),
(2) Date: Apr. 17, 2017

(87) PCT Pub. No.: WO2016/061465
PCT Pub. Date: Apr. 21, 2016

(65) Prior Publication Data
US 2017/0247767 A1    Aug. 31, 2017

Related U.S. Application Data

(60) Provisional application No. 62/065,122, filed on Oct. 17, 2014.

(51) Int. Cl.
*C12Q 1/68* (2018.01)
*C12Q 1/6886* (2018.01)
*C12Q 1/70* (2006.01)

(52) U.S. Cl.
CPC ........... *C12Q 1/6886* (2013.01); *C12Q 1/708* (2013.01); *C12Q 2600/154* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

2013/0303826 A1    11/2013   Jurisica et al.
2014/0271455 A1*   9/2014   Pfeifer .................. C12Q 1/6886
                                                    424/1.11

FOREIGN PATENT DOCUMENTS

| CN | 103857796 A | 6/2014 |
|---|---|---|
| EP | 2757154 A1 | 7/2014 |
| WO | WO 200070090 A1 | 11/2000 |
| WO | WO 2013039394 A1 | 3/2013 |

OTHER PUBLICATIONS

Ambros, V. (2004) "The functions of animal microRNAs." Nature, 431(7006), pp. 350-355.
Babu et al. (2011) "A miR-centric view of head and neck cancers." *Biochim Biophys Acta*, 1816 (1), 67-72.
Betel et al. (2008) "The microRNA.org resource: targets and expression." Nucleic Acids Res., 36, D149-D153.
Boyle et al. (1994) "Gene mutations in saliva as molecular markers for head and neck squamous cell carcinomas." Am. J. Surg., 168(5), pp. 429-432.
Croce, C. M. (2009) "Causes and consequences of microRNA dysregulation in cancer." *Nat Rev Genet*, 10 (10), pp. 704-714.
Friedman et al. (2009) "Most mammalian mRNAs are conserved targets of microRNAs." Genome Res., 19,92-105.
Gangaraju et al. (2009) "MicroRNAs: key regulators of stem cells." *Nat Rev Mol Cell Biol*, 10(2), pp. 116-125.
Garzon et al. (2010) "Targeting microRNAs in cancer: rationale, strategies and challenges." Nat. Rev. Drug. Discov., 9(10), pp. 775-789.
Ha et al. (2006) "Promoter methylation and inactivation of tumour-suppressor genes in oral squamous-cell carcinoma." *Lancet Oncol*, 7 (1), pp. 77-82.
Hildebrandt et al. (2010) "Hsa-miR-9 methylation status is associated with cancer development and metastatic recurrence in patients with clear cell renal cell carcinoma." *Oncogene*, 29 (42), pp. 5724-5728.
Iorio et al. (2010) "Interplay between microRNAs and the epigenetic machinery: an intricate network." *Biochem Biophys Acta*, 1799 (10-12), pp. 694-701.
Iorio et al. (2012) "MicroRNA dysregulation in cancer: diagnostics, monitoring and therapeutics. A comprehensive review." *EMBO Mol Med*, 4 (3), pp. 143-159.
Jemal et al. (2009) "Cancer statistics, 2009." *CA Cancer J Clin*, 59 (4), pp. 225-249.
Jones et al. (2007) "The epigenomics of cancer." *Cell*, 128 (4), pp. 683-692.
Krek et al (2005) "Combinatorial microRNA target predictions." Nature Genet., 37, pp. 495-500.
Langevin et al. (2010) "MicroRNA-137 promoter methylation in oral rinses from patients with squamous cell carcinoma of the head and neck is associated with gender and body mass index." Carcinogenesis, vol. 31, No. 5, pp. 864-870.

(Continued)

*Primary Examiner* — Katherine D Salmon
(74) *Attorney, Agent, or Firm* — Lathrop GPM LLP

(57) ABSTRACT

Disclosed is a diagnostic panel of methylated genomic loci encoding microRNA (mgmiR) markers that demonstrated 90% sensitivity and 100% specificity in the detection of head and neck squamous cell carcinoma (HNSCC). These results represent the first use of quantitative MS-PCR for the detection of mgmiRs. In addition this panel demonstrates the ability to detect hypermethylation in the adjacent mucosa of cancer patients, suggesting its utility in early detection. This panel is also capable of detecting cancer by using saliva, blood and FNA tissue samples.

4 Claims, 11 Drawing Sheets

Specification includes a Sequence Listing.

(56) References Cited

OTHER PUBLICATIONS

Lee et al. (1993) "The C. elegans heterochronic gene lin-4 encodes small RNAs with antisense complementarity to lin-14." Cell, 1993, 75(5), pp. 843-854.

Lewis et al. (2003) "Prediction of mammalian microRNA targets." Cell, 115, pp. 787-798.

Lujambio et al.(2008) "A microRNA DNA methylation signature for human cancer metastasis." *Proc Natl Acad Sci*, 105 (36), pp. 13556-13561.

Minor et al. (2012) "Methylation of microRNA-9 is a specific and sensitive biomarker for oral and oropharyngeal squamous cell carcinomas." Oral Oncol., 48(1), pp. 73-78.

PCT/US2015/055958 International Search Report & Written Opinion dated Jan. 20, 2016, 9 pp.

PCT/US2015/056958 International Search Report & Written Opinion dated Dec. 15, 2015, 8 pp.

Roh et al. (2012) "Tissue imprint for molecular mapping of deep surgical margins in patients with head and neck squamous cell carcinoma." *Head Neck*, 34 (11), pp. 1529-1536.

Rosenfeld et al. (2008) "MicroRNAs accurately identify cancer tissue origin." *Nat Biotechnol*, 26 (4), pp. 462-469.

Saito et al. (2006) "Epigenetic activation of tumor suppressor microRNAs in human cancer cells." *Cell Cycle*, 5 (19), pp. 2220-2222.

Saito et al. (2006) "Specific activation of microRNA-127 with downregulation of the proto-oncogene BCL6 by chromatin-modifying drugs in human cancer cells." *Cancer Cell*, 9 (6), pp. 435-443.

Siegel et al. (2013) "Cancer statistics, 2013." *CA Cancer J Clin*, 63 (1), pp. 11-30.

Watson et al. (1953) "Molecular structure of nucleic acids; a structure for deoxyribose nucleic acid." Nature, 171 (4356), pp. 737-738.

Worsham et al. (2012) "Molecular characterization of head and neck cancer: how close to personalized targeted therapy?" Mol Diagn Ther., 16(4), pp. 209-222.

Worsham et al. "Epigenetic modulation of signal transduction pathways in HPV-associated HNSCC." Otolaryngol Head Neck Surg., 149(3), pp. 409-416.

Chinese Patent Application No. 201580056428.0, Office Action dated Feb. 7, 2020, 12 pages.

Langevin (2010) "MicroRNA-137 promoter methylation in oral rinses from patients with squamous cell carcinoma of the head and neck is associated with gender and body mass index", Carcinogenesis, 31:5, pp. 864-870.

\* cited by examiner

| SEQ ID | primer sequences of the qMS-PCR (mgmiR assay) | |
|---|---|---|
| #1 | mgmir124-1F1 | GAGTTGCGGCGGGGAGGA |
| #2 | mgmir124-1R1 | CGACGCGTATACGTACGCACTAACAA |
| #3 | mgmir124-2F1 | TATTAGAGGGGTAATTAATTTGGATTTACGTCG |
| #4 | mgmir124-2R1 | ACGATACGTATACCTACGTATACATATACATAT |
| #5 | mgmiR124-3F1 | CGAAGACGTTTGAGCGTTCG |
| #6 | mgmiR124-3R1 | GAACGTCGAAACCAAAATCG |
| #7 | mgmiR137F1 | TAGCGGTAGCGGTAGTAGC |
| #8 | mgmiR137R1 | ACCCAAAAATACCCGTCACCG |
| #9 | mgmir9-1F1 | TTCGTTGACGGGCGATCGG |
| #10 | mgmir9-1R1 | ACTATCGCCGCCTCTTCCAC |

Sequence was generated from human ensemble database; human chromosome GRCH38.

SEQ ID: #11

Sequence of genomic loci encoding miR124-1 (reverse strand)

>chromosome 8: 9903388---9904472 (GRCh38)

CAGCCCCATTCTTGGCATTCACCGCGTGCCTTAATTGTATGGACATTTAAATCAAGGTCC
GCTGTGAACACGGAGAGAGAGGCCTTTCTCCTGAGGAAGGAAAGGAGGAAGGAAGGAAGG
AAAGGTGAAAGAAAGGAAGAGGGGTGGGTAGAAGATGGAATAAGAAAACCAGGAAAAAGA
AATAAAAAGCGGCGCGTGTGCGTGCGCACTGACAGCGGGGAGAGGGATGGGGGTGGGGAA
CGCCGGAGGAAGGGACCACAGCATCCTCCCCGCCGCAGCTCCCCAATCACACAGACAAT
GAGATAACAGCGACGTCTTCCAAAGGCTCTTTGTTCTCCCCCATCCTTTCGCATCCAGGC
TTTTTCCTGCAAAGCGGAGGGGGTGGAGGGATGGGGGTGTGGGTGGAAGTGGGAGACGGA
GGGGTGCCTCCCCCGTGTTAATTACCCCGGCTCCCCTCGCCCCTTTCCCCGCGCCTCGCC
TCCCCTGCAGCTCCAGACAATGAAAAAACAACATCGACCCCACCTCGCCCCAGCGCAGCA
ACCCACCCACCCATGTCGCCCTCTGCTTCGCCCAGGAAACTGAAGGGGACTAGGAGGAGG
AAGAAGAGAGCGAAGGACAAGGAGAGCAGCGGGGACTCGGCAGCGGCAGCCGGGCAGGG
CGCGCGGCCGCCGCCTCTTTACCTCCATCGCTGAGTGGGGCGCAGCCGGGCCGGGCGTG
CCGCAGGGCGAGTTGCCGCGGTCCGGGGCTGGGACCTGGGGATTCAGCCTTCCGGAACT
CGCCTGCTGCAGTCCTCTCGCTCAGGTCCCAAGTGGTGGAGGGGGGAAAGGAAGAGAGAC
GAGAGAGAGAGAGACAGAGAGAGAGAGAGAGAGGAAGAAGAAGAAGAAGAAGAAAAAA
AAACCATAAGAGCGAGGCCCATCTGGCCCCTCATCAGCTTTGTCAAGTCTTGCATACGCT
AAAATGCTAATGACCTAGATAGCTCATGCAAAATGCAGCAGGGAGGGCGGGAGCGAGGGA
GGTGGGAGGGAGGAAGAGAGAGGAGTGCAGGGGGGAGGGAGGGAGGAGAGGCGGAGGGAG
GGAGA

FIGURE 12

SEQ ID: #12

Sequence of genomic loci encoding miR124-2 (forward strand)

>chromosome 8:64378149---64379257 (GRCh38)

TCGACCACGCCGTAGGGGACGCCGTGAAAAGAGCCGTCGCGCCCGCTGCCTCCTGCCCGC
TGCGCAGAGGGCTCCGCCCGTAGAGGTCAACTTCCCTCACCCTTTTCTCTCTCCTGCTTG
CCCTCCCTCCGCCCGGCCCAGGCGCTTCCAGCCCCAGACTGTGGCCACTGGCTGAGGAGT
GCGAGTCGGCTGCGCTGCCCTGAGCCTAATCCCTCTTCCGGGCCCAGACCCGAGGTCCGC
GCTCCTGGGCAGTGGGGAAGCTTTAGTGAGCAGGCTTTTCTCTCCGCAGCAAACTTGTAG
CCAGACCAGATGGGCCGCCCAGCTCTCTCGGGACTAGGCAGGTGCGGATGAGTTAATTTT
TCCGCATTACAAAGAAAGATGACCCAGCCCGCCCTTGGACTCTCTTTTCCCAAAATCTCC
CAACCAAACCCGCGGTAACGTTATCAAAGGACACAGAGCCCAGGCATATCTGTGTGTTTA
TCTTACAGGCACACACGCATGGTTTTCTCTTTTATATGCTAGATTTCATCCCTGACAGCA
GAAAATGATTGGCAATGGTTATGACGGAGAACATGCAATAGCGTGGTCCTTAAAAACCTG
CCATTCCTTACAAGTGCCTTAGAAAGGATTCAGGGCGAACCAACTGGGTTAATTGCATTC
AGTAAAATAACACGATTACAAAATTAGATCTGTACCAGAGGGGTAATTAACTTGGATCCA
CGCCGTCATTTGAAAACTAGATTTATAGGCTTATGTATGTTTTTAGGCGTGTGCTGTAAA
TGGCATGGAGATATATGCATATGTATACGCAGGCACACGCACCGTCTACACTTCCACGGA
ACAGACTAATTAACAGCGGCTCTGGCAGATGTGTCAGAGATGAGCAGAGACAGGAGCTGG
GCTTATGAGTTATGACTCTAGGGGTAGAGACTCAGAGCGGAGAGAGGGGATGGGCAGGG
AGAGAAGAGTGGTAATCGCAGTGGGTCTTATACTTTCCGGATCAAGATTAGAGGCTCTGC
TCTCCGTGTTCACAGCGGACCTTGATTTAATGTCATACAATTAAGGCACGCGGTGAATGC
CAAGAGCGGAGCCTACGGCTGCACTTGAA

SEQ ID: #13

Sequence of genomic loci encoding miR124-3 (forward strand)

>chromosome 20:63177500---63178586 (GRCh38)

CTCGGGGAGGCAGCGGCGGGGCCGGTGTCCGGGTGACGTCACCGCGCGCCCCAGTGATAA
TCGGCCGGTGCCGGAGCGGAGCGCGGATACGCGCGGAGGCAACGGCGACGGCGGCGGCGG
CGGCGGGCGCGGGGACAGTTGCATCGGGGCCGGGCCGGGCTAGCAGGAGCTGGGCGCCTG
CAGCGTGGACCCCGTGGACACTCGGCTCGCAGCCGGCCTGCGGCGCTCGGGGACTTGCCT
GGCTCCCTTCTCGGGGTTCCCGCGCCCTTCTCCGCCCAGGGCAGCAGCGCGCGGGGCCCC
CGGGAGCCGAAGAGCAGGCGGGAACTGGCGGCGGCGCGGGAGGCGCAGGGAGCGGAGGCG
GCAGCAGCGGCTCCCGCCGGGACTGGTAATTACGCTCGGGGCCGGGCCGGGGCGAGCCGG
GCAAGCGGCCTCTCTGGGTCTCCCCGTCTTTCTCTCCACGAACAGCTCGAGCGCCTTCTC
GCGGGCCCGCTGCGCGCGGAGAGGACGAGCTCGCTGGGTTGTAAAAAGAGACGAGTTTTC
ATCTTTGAGCATCGAGATTCGTTCTTTTAACCGCATTCGGTGCGCGCTCCTGGGTCGGCA
CGGGCAGGGCGACGGCAGGGAAGGCAGCTGCGGAGGAGCTCGCGCCGCCCAGTCGGAGC
GGTTCTGCGCCCCTCGGAGCCCCGCGGGAGGCGGCCGGGTGCGCACGCGCTCACCACCCC
CACCCCCGGAATCCGTCTTCGCGATTCCCGGGCGCCCAGCTCCAGGAACGCCCGGAGGG
ACGCACTTGGGGGCCCACTCTCTGCCGCGGAAAGGGGAGAAGTGTGGGCTCCTCCGAGTC
GGGGGCGGACTGGGACAGCACAGTCGGCTGAGCGCAGCGCCCCGCCCTGCCCGCCACGC
GGCGAAGACGCCTGAGCGTTCGCGCCCCTCGGGCGAGGACCCCACGCAAGCCCGAGCCGG
TCCCGACCCTGGCCCCGACGCTCGCCGCCCGCCCCAGCCCTGAGGGCCCCTCTGCGTGTT
CACAGCGGACCTTGATTTAATGTCTATACAATTAAGGCACGCGGTGAATGCCAAGAGAGG
CGCCTCC

FIGURE 12 (cont.)

SEQ ID: #14

Sequence of genomic loci encoding miR137 (reverse strand)

>chromosome 1:98046070---98047171 (GRCh38)

TGCCGCTGGTACTCTCCTCGACTACGCGTATTCTTAAGCAATAACAACGTAATCCGTATT
ATCCACCCAAGAATACCCGTCACCGAAGAGAGTCAGAGGACCAAGCTGCCGCTGCCGCTG
CTACCGCTGCCGCTGCTACCGCTGCCGCTGCTACTGCCGCCGCCGCCGCCACCAGAACTC
TTGCTGCTCGCTGAGCCCGCCCCTGCCTGGGGATGGGCTGAGCTTGACCGGGACCATAAA
TCCATAACTCGATTTCCCTAAAGAAGGATCCAAAGCTGTGCTCGGCTGCTTCCTGCCCAA
ATCCAAATGGCCGCTCTATTTCCAATTCTGAAAGACAAATCACAAAATCAAATACTTAAC
ACAGAAGAGTGCTGTCTTTCCAGTGAGGAGGGAAGATGTGGCAAGGCTTTTTGGGCACAA
GTGGGAGTGACAAGTAACCTTCAGTTTACCTGGTGCTCTCCCAGTGCTTTCCTCTGCACT
TCTCTGCTTGGTACCCAGTCTGGTCTCGGCCAGTCCACTCTAGGTGGTATGATTGAGTGC
CATGGCGGCCAGAGAACCCTGTAAGAGACGTGAATAGTTACCCACACAAATACAAATATA
TTTGCCTAGACGGCTTTGGGAAGAAGTGAGGCTTAAATAAAGATAGGTCATGCATGGGTG
AAATTTTCAGTAGTGTGTTTTGGAAATGCACTTTTCTCAAGCCCAAGATCATGGAAAATA
AACACTCATTCAATTTACTACTTGAAATCAAATACTTATAGATGTACAAAAATAGGCGTC
TTTCCTTTGAAGGCCTTATAGCTATACAACATAATGATTTTTAAAGAAAAAAAAAGCTT
GAAGGCACACAGTAATTAAACCCATTTTCCATAGTGTCAAAACTCACTGAGTTGACAAGC
TGGTAGACTTTCTATGATTTAAGCATCATTTTATATCACTACAATGTTTAATTTCATAGC
ACACTTTTAAAATATATACTATAAATGCATTGCTGTACAGCTGTTGTGGACACCTCTACA
GAAAAACCTTTGAAGCTCTGTGTTCATAAATATTATTTTAAGAAGAAAAAGCCAATAAAA
ACTCATTTGCAAAGTGACTGTA

SEQ ID: #15

Sequence of genomic loci encoding miR9-1 (reverse strand)

>chromosome 1: 156420331---156421438 (GRCh38)

GCGCAGTGTATGGGGTTATTTTTACTTTCGGTTATCTAGCTTTATGAAGACTCCACACCA
CTCATACAGCTAGATAACCAAAGATAACAACCAACCCCGCCTCCTGGCTGCTGTCGCCGC
CTCTTCCACGCAGCCTCCCGGCCGCCGCCGCCGCCAGCACCTCCGCAGCTTCCCGGTCGC
CCGTCAGCGGGAGTAGGAGGGAAGGGACACGAGTGGAGTTGAGGGGGAGGGTGAAGAGAG
AAATGAAGTCCGAGACAAAACAACAACAAAAACCTCAGACACGGAGATACAGACACGACA
GAGACCGAAAAAGGCGTGGAAAGGACGCGATGACCCGTGGCGTCGAAGTCGGGGAGTTGA
CCCCGATCCAGACCCAAAAAGTTTCTGGTGCCCCATTTCCCGCTCTCCCATTCGGGCCAG
GAGCAGGAGTTCCGCTGGTCCCAGGTGGAAGGGACGCGCGGGCTTTTCGTGCCACCCGGG
AAGACCGCAGCGACCCAGGCAGAGGCCTCCCCAGCCTCGCCGGGTCTCCACTGCCCTTCT
CTGGAAGATCGAGGGCGCATCCGACAGCCAGAGCCCTGCCTTCGGCGGAGCCCGAGCCTG
GCGCGGGATGGAAATGGGGAGCCGCGGTGCCGGCCCGGCCACGTCGCCAACTCAGAAAGG
CGTTGGAAGCGAAGCGGAGCCCTTGTGGGGAAAGAGCCGGATTCAAGAGGCCGACTAAA
AGGGGAAATGGGCAGCCAAACCCCGGAGGTAAAAACCCCAGAGATGTCCTAATAGGAAGC
AGGGAAATCCCGGCGACCCAAAGAGAGAGGAAAGGCTGTGGGGGCGGGTGGGGCGACC
CAGAGACTCCCAAGCGAGTCTCTCAAGGAGAGAAGGAAACAGCAGAGACCCCACCCGGGA
AGAGATCCGGGAGAGTACCCATGAGAGGGCGGAGGGGAGGAAAGCAGAGGGCGACAGGG
CAGGTGACCAGAGTCCCAGGCCCTGCAGAGCCCCGGATAAACGGCTTTGTTCAAAGAGGA
CCAGAGATCACCCAGGGTTGTGAAAATGGCCGGGGGTTCGAGGCGAGCGGTGCTCTAGGG
GTGGGAAAGGGGTGCGATCAGGAACGGG

FIGURE 12 (cont.)

SEQUENCE LISTING

```
<160> NUMBER OF SEQ ID NOS: 15

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
gagttgcggc ggggagga                                                 18

<210> SEQ ID NO 2
<211> LENGTH: 26
<212> TYPE: DNA
<213> ORGANISM: Artificial Sequence
<220> FEATURE:
<223> OTHER INFORMATION: synthetic

<400> SEQUENCE: 2
cgacgcgtat acgtacgcac taacaa                                        26

<210> SEQ ID NO 3
<211> LENGTH: 33
<212> TYPE: DNA
<213> ORGANISM: Artificial Sequence
<220> FEATURE:
<223> OTHER INFORMATION: synthetic

<400> SEQUENCE: 3
tattagaggg gtaattaatt tggatttacg tcg                                33

<210> SEQ ID NO 4
<211> LENGTH: 33
<212> TYPE: DNA
<213> ORGANISM: Artificial Sequence
<220> FEATURE:
<223> OTHER INFORMATION: synthetic

<400> SEQUENCE: 4
acgatacgta tacctacgta tacatataca tat                                33

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
cgaagacgtt tgagcgttcg                                               20
```

```
<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
gaacgtcgaa accaaaatcg                                                  20

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
tagcggtagc ggtagtagc                                                   19

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
acccaaaaat acccgtcacc g                                                21

<210> SEQ ID NO 9
<211> LENGTH: 19
<212> TYPE: DNA
<213> ORGANISM: Artificial Sequence
<220> FEATURE:
<223> OTHER INFORMATION: synthetic

<400> SEQUENCE: 9
ttcgttgacg ggcgatcgg                                                   19

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
actatcgccg cctcttccac                                                  20

<210> SEQ ID NO 11
<211> LENGTH: 1085
<212> TYPE: DNA
<213> ORGANISM: Homo sapiens

<400> SEQUENCE: 11
cagccccatt cttggcattc accgcgtgcc ttaattgtat ggacatttaa atcaaggtcc      60
gctgtgaaca cggagagaga ggcctttctc ctgaggaagg aaaggaggaa ggaaggaagg     120
aaaggtgaaa gaaaggaaga ggggtgggta gaagatggaa taagaaaacc aggaaaaaga     180
aataaaaagc ggcgcgtgtg cgtgcgcact gacagcgggg agagggatgg gggtggggaa     240
cgccggagga agggaccaca gcatcctccc cgccgcagct cccccaatca cacagacaat     300
gagataacag cgacgtcttc caaaggctct ttgttctccc ccatccttc gcatccaggc      360
```

```
tttttcctgc aaagcggagg gggtggaggg atggggtgt gggtggaagt gggagacgga      420
ggggtgcctc ccccgtgtta attacccgg ctcccctcgc cctttcccc gcgcctcgcc       480
tccctgcag ctccagacaa tgaaaaaaca acatcgaccc cacctcgccc cagcgcagca      540
acccacccac ccatgtcgcc ctctgcttcg cccaggaaac tgaaggggac taggaggagg     600
aagaagagag cgaaggacaa ggagagcagc ggggactcgg cagcggcagc cggggcaggg    660
cgcgcggccg ccgcctcttt acctccatcg ctgagtgggg gcgcagccgg gccgggcgtg    720
ccgcagggc gagttgccgc ggtccggggc tgggacctgg ggattcagcc ttccggaact     780
cgcctgctgc agtcctctcg ctcaggtccc aagtggtgga ggggggaaag gaagagagac    840
gagagagaga gagacagaga gagagagaga gagaggaaga agaagaagaa gaagaaaaaa    900
aaaccataag agcgaggccc atctggcccc tcatcagctt tgtcaagtct tgcatacgct    960
aaaatgctaa tgacctagat agctcatgca aaatgcagca gggagggcgg gagcgaggga   1020
ggtgggaggg aggaagagag aggagtgcag gggggaggga gggaggagag gcggagggag   1080
ggaga                                                               1085

<210> SEQ ID NO 12
<211> LENGTH: 1109
<212> TYPE: DNA
<213> ORGANISM: Homo sapiens

<400> SEQUENCE: 12
tcgaccacgc cgtaggggac gccgtgaaaa gagccgtcgc gcccgctgcc tcctgcccgc     60
tgcgcagagg gctccgcccg tagaggtcaa cttccctcac ccttttctct ctcctgcttg   120
ccctccctcc gcccggccca ggcgcttcca gccccagact gtggccactg gctgaggagt   180
gcgagtcggc tgcgctgccc tgagcctaat ccctcttccg ggcccagacc cgaggtccgc   240
gctcctgggc agtggggaag ctttagtgag caggcttttc tctccgcagc aaacttgtag   300
ccagaccaga tgggccgccc agctctctcg ggactaggca ggtgcggatg agttaatttt   360
tccgcattac aaagaaagat gacccagccc gcccttggac tctctttcc caaaatctcc    420
caaccaaacc cgcggtaacg ttatcaaagg acacagagcc caggcatatc tgtgtgttta    480
tcttacaggc acacacgcat ggttttctct tttatatgct agatttcatc cctgacagca   540
gaaaatgatt ggcaatggtt atgacggaga acatgcaata gcgtggtcct taaaaacctg   600
ccattcctta caagtgcctt agaaaggatt cagggcgaac caactgggtt aattgcattc   660
agtaaaataa cacgattaca aaattagatc tgtaccagag gggtaattaa cttggatcca   720
cgccgtcatt tgaaaactag atttataggc ttatgtatgt ttttaggcgt gtgctgtaaa   780
tggcatggag atatatgcat atgtatacgc aggcacacgc accgtctaca cttccacgga   840
acagactaat taacagcggc tctggcagat gtgtcagaga tgagcagaga caggagctgg   900
gcttatgagt tatgactcta ggggtagaga ctcagcgg agagagggg atgggcaggg       960
agagaagagt ggtaatcgca gtgggtctta tactttccgg atcaagatta gaggctctgc  1020
tctccgtgtt cacagcggac cttgatttaa tgtcatacaa ttaaggcacg cggtgaatgc  1080
caagagcgga gcctacggct gcacttgaa                                    1109

<210> SEQ ID NO 13
<211> LENGTH: 1087
<212> TYPE: DNA
<213> ORGANISM: Homo sapiens

<400> SEQUENCE: 13
```

| | |
|---|---|
| ctcggggagg cagcggcggg gccggtgtcc gggtgacgtc accgcgcgcc ccagtgataa | 60 |
| tcggccggtg ccggagcgga gcgcggatac gcgcggaggc aacggcgacg gcggcggcgg | 120 |
| cggcgggcgc ggggacagtt gcatcggggc cgggccgggc tagcaggagc tgggcgcctg | 180 |
| cagcgtggac cccgtggaca ctcggctcgc agccggcctg cggcgctcgg ggacttgcct | 240 |
| ggctcccttc tcggggttcc cgcgcccttc tccgcccagg gcagcagcgc gcggggcccc | 300 |
| cgggagccga agagcaggcg ggaactggcg gcggcgcggg aggcgcaggg agcggaggcg | 360 |
| gcagcagcgg ctcccgccgg gactggtaat tacgctcggg gccgggccgg ggcgagccgg | 420 |
| gcaagcggcc tctctgggtc tccccgtctt tctctccacg aacagctcga gcgccttctc | 480 |
| gcgggcccgc tgcgcgcgga gaggacgagc tcgctgggtt gtaaaaagag acgagttttc | 540 |
| atctttgagc atcgagattc gttcttttaa ccgcattcgg tgcgcgctcc tgggtcggca | 600 |
| cgggcagggc gacggcaggg gaaggcagct gcggaggagc tcgcgccgcc cagtcggagc | 660 |
| ggttctgcgc ccctcggagc cccgcgggag gcggccgggt gcgcacgcgc tcaccacccc | 720 |
| caccccggga atccgtcttc gcgattcccg ggcgccccag ctccaggaac gcccggaggg | 780 |
| acgcacttgg gggcccactc tctgccgcgg aaagggagga agtgtgggct cctccgagtc | 840 |
| gggggcggac tgggacagca cagtcggctg agcgcagcgc ccccgccctg cccgccacgc | 900 |
| ggcgaagacg cctgagcgtt cgcgcccctc gggcgaggac cccacgcaag cccgagccgg | 960 |
| tcccgaccct ggccccgacg ctcgccgccc gccccagccc tgagggcccc tctgcgtgtt | 1020 |
| cacagcggac cttgatttaa tgtctataca attaaggcac gcggtgaatg ccaagagagg | 1080 |
| cgcctcc | 1087 |

<210> SEQ ID NO 14
<211> LENGTH: 1102
<212> TYPE: DNA
<213> ORGANISM: Homo sapiens

<400> SEQUENCE: 14

| | |
|---|---|
| tgccgctggt actctcctcg actacgcgta ttcttaagca ataacaacgt aatccgtatt | 60 |
| atccacccaa gaatacccgt caccgaagag agtcagagga ccaagctgcc gctgccgctg | 120 |
| ctaccgctgc cgctgctacc gctgccgctg ctactgccgc cgccgccgcc accagaactc | 180 |
| ttgctgctcg ctgagcccgc ccctgcctgg ggatgggctg agcttgaccg ggaccataaa | 240 |
| tccataactc gatttcccta agaaggatc caaagctgtg ctcggctgct tcctgcccaa | 300 |
| atccaaatgg ccgctctatt tccaattctg aaagacaaat cacaaaatca atacttaac | 360 |
| acagaagagt gctgtctttc cagtgaggag ggaagatgtg gcaaggcttt tgggcacaa | 420 |
| gtgggagtga caagtaacct tcagtttacc tggtgctctc ccagtgcttt cctctgcact | 480 |
| tctctgcttg gtacccagtc tggtctcggc cagtccactc taggtggtat gattgagtgc | 540 |
| catggcggcc agagaaccct gtaagagacg tgaatagtta cccacacaaa tacaaatata | 600 |
| tttgcctaga cggctttggg aagaagtgag gcttaaataa agataggtca tgcatgggtg | 660 |
| aaattttcag tagtgtgttt tggaaatgca cttttctcaa gcccaagatc atggaaaata | 720 |
| aacactcatt caatttacta cttgaaatca aatacttata gatgtacaaa ataggcgtc | 780 |
| tttcctttga aggccttata gctatacaac ataatgattt ttaaagaaaa aaaaaagctt | 840 |
| gaaggcacac agtaattaaa cccatttttcc atagtgtcaa aactcactga gttgacaagc | 900 |
| tggtagactt tctatgattt aagcatcatt ttatatcact acaatgttta atttcatagc | 960 |

-continued

```
acacttttaa aatatatact ataaatgcat tgctgtacag ctgttgtgga cacctctaca   1020
gaaaaacctt tgaagctctg tgttcataaa tattatttta agaagaaaaa gccaataaaa   1080
actcatttgc aaagtgactg ta                                            1102

<210> SEQ ID NO 15
<211> LENGTH: 1108
<212> TYPE: DNA
<213> ORGANISM: Homo sapiens

<400> SEQUENCE: 15
gcgcagtgta tggggttatt tttactttcg gttatctagc tttatgaaga ctccacacca     60
ctcatacagc tagataacca aagataacaa ccaaccccgc ctcctggctg ctgtcgccgc    120
ctcttccacg cagcctcccg gccgccgccg ccgccagcac ctccgcagct tcccggtcgc    180
ccgtcagcgg gagtaggagg gaagggacac gagtggagtt gaggggagg gtgaagagag    240 aaatgaagtc cgagacaaaa caacaacaaa aacctcagac acggagatac agacacgaca    300
gagaccgaaa aaggcgtgga aaggacgcga tgacccgtgg cgtcgaagtc ggggagttga    360
ccccgatcca gacccaaaaa gtttctggtg ccccatttcc cgctctccca ttcgggccag    420
gagcaggagt tccgctggtc ccaggtggaa gggacgcgcg ggcttttcgt gccacccggg    480
aagaccgcag cgacccaggc agaggcctcc ccagcctcgc cgggtctcca ctgcccttct    540
ctggaagatc gagggcgcat ccgacagcca gagccctgcc ttcggcggag cccgagcctg    600
gcgcgggatg gaaatgggga gccgcggtgc cggcccggcc acgtcgccaa ctcagaaagg    660
cgttggaagc gaagcggagc ccttgtgggg gaaagagccg gattcaagag gccgactaaa    720
aggggaaatg ggcagccaaa ccccggaggt aaaaaccca gagatgtcct aataggaagc    780
agggaaatcc cggcgaccca aagagagagg aaaggctgtg gggggcgggt ggggcgacc    840 cagagactcc caagcgagtc tctcaaggag agaaggaaac agcagagacc ccacccggga    900
agagatccgg gagagtaccc atgagagggg cggaggggga gaaagcagag ggcgacaggg    960
caggtgacca gagtcccagg ccctgcagag ccccggataa acggctttgt tcaaagagga   1020
ccagagatca cccaggggttg tgaaaatggc cggggggttcg aggcgagcgg tgctctaggg   1080
gtgggaaagg ggtgcgatca ggaacggg                                      1108
```

BIOMARKERS FOR HEAD AND NECK CANCER AND METHODS OF THEIR USE

RELATED APPLICATION

This application claims priority to U.S. Provisional Patent Application No. 62/065,122, filed Oct. 17, 2014, which is incorporated by reference into the present application in its entirety and for all purposes.

BACKGROUND

1. Field of the Invention

The instant disclosure relates to detection and treatment of cancers. More particularly, it relates to the use of biomarkers for detecting, treating and monitoring head and neck cancer.

2. Description of Related Art

Head and neck squamous cell carcinoma (HNSCC) represents approximately 90% of all head and neck cancer and 5% of all malignancies. See Jemal et al. (2009) and Worshem et al. (2013). Oral cavity and pharynx cancers alone were the eighth most common cancer among males in the United States in 2008, and HNSCC was seen in more than 48,000 new patients in 2009 in the United States (Jemal et al.). HNSCC has also seen an increasing rate of prevalence over the past 30 years. See Worsham et al. (2013). Despite the advancements in medical and cancer therapy, the survival rates for patients with HNSCC have been fairly stagnant. See Siegel et al. (2013). This low survival rate is in stark contrast to the increase in survival rates of many other cancers. One of the main reasons for the poor prognosis of HNSCC is that more than half of HNSCC patients have advanced to either locoregional or metastatic stages of the disease at the time of diagnosis. Therefore, early detection may be key to improving survival rates in the future. No effective methods have been reported for early detection of head and neck cancer.

SUMMARY

The present disclosure advances the art by providing methods for early detection of certain types of cancer. More particularly, a diagnostic panel of methylated genomic loci encoding microRNA (mgmiR) markers is disclosed which shows 90% sensitivity and 100% specificity in the detection of head and neck squamous cell carcinoma (HNSCC). These results represent the first use of quantitative MS-PCR for the detection of methylation level using mgmiR markers. In addition, this panel of microRNAs has demonstrated the ability to detect hypermethylation in the adjacent mucosa of cancer patients, suggesting its utility in early detection. This panel may also be used for detecting cancer by using saliva, blood and fine-needle aspiration (FNA) tissue samples, among others.

In one embodiment, a method is disclosed for detecting cancer in a subject, which may include (a) measuring methylation level of at least one genomic locus encoding at least one microRNA selected from the group consisting of miR124-1, 124-2, 124-3, 137 and 9-1, and (b) comparing the methylation level obtained from the subject with that of a corresponding genomic locus encoding the same microRNA from an individual known to be free from the cancer (the latter also being referred to as "base methylation level" or "base level" in this disclosure). The disclosed method may further include providing a diagnosis where a significantly higher methylation level of the DNA fragment in the subject as compared to the base methylation level is indicative of cancer or pre-cancer.

For purpose of this disclosure, the term "significantly higher" may mean at least 20%, 40%, 50%, 80%, 100%, 150%, 200% or even higher.

In another embodiment, a method for detecting cancer may include: (a) preparing a DNA extract from a tissue or a body fluid of the subject, where the DNA extract contains at least one first DNA fragment encompassing at least one genomic locus encoding at least one microRNA selected from the group consisting of miR124-1, 124-2, 124-3, 137 and 9-1, (b) generating a second DNA fragment by polymerase chain reaction (PCR) using as a template the first DNA fragment and using as primers oligonucleotides specific to methylated DNA, (c) measuring the level of the second DNA fragment generated in step (b), and (d) comparing the level of the second DNA fragment with a base level, where a higher level of the second DNA fragment as compared to the base level is indicative of cancer or pre-cancer. In one aspect, the base level is the level of a corresponding DNA fragment generated by the same manner from the same tissue or body fluid of an individual known to be free from the cancer.

In another embodiment, the primers used for the qMS-PCR are primer pairs selected from the group consisting of SEQ ID Nos. 1-10. "F" indicates forward primer, "R" indicates reverse primer.

In one aspect, the disclosed methods may be suitable with or without modification for early detection of cancer (or pre-cancer). Examples of cancer may include but are not limited to head and neck squamous cell carcinoma (HNSCC), esophageal cancer, lung cancer, cervical cancer, breast cancer, colon cancer, rectal cancer, stomach cancer, pancreas cancer, liver cancer, gallbladder cancer, bile duct cancer, small intestine cancer, urinary tract cancer, female genital tract cancer, male genital tract cancer, endocrine gland cancer, skin cancer, hemangiomas, melanomas, sarcomas, brain tumor, nerve cancer, eye tumor, meninges cancer, or solid tumors from hematopoietic malignancies, among others.

In another embodiment, the at least one microRNA or the DNA fragment encoding the at least one microRNA may be isolated from a tissue or body fluid selected from the group consisting of a head tissue, a neck tissue, mouth swap, nose swap, saliva, sputum, blood, serum, Cerebrospinal fluid (CSF), urine, FNA tissue, other body fluids, or combination thereof.

The five genomic loci encoding microRNAs (also referred to as "mgmiRs" markers) may also be used as a panel, where at least two, three, four, or all five need to show significantly higher level of methylation in the subject as compared to the base level before a positive call of cancer or pre-cancer is made.

In another embodiment, the base level may be a preset value established by averaging the levels obtained from two or more individuals known to be free from the cancer. By way of example, preset values are used in the Examples of the present disclosure but may be modified by one of skills in the art.

In another embodiment, a method is disclosed for detecting cancer in a subject, which may include (a) measuring the level of at least one microRNA in a tissue or body fluid isolated from the subject, wherein at least one microRNA is selected from the group consisting of miR124-1, 124-2, 124-3, 137 and 9-1 and (b) comparing the level of the at least one microRNA with a base level, said base level being the level of the same microRNA from the same tissue or body fluid of an individual known to be free from the cancer, where a significantly lower level of the at least one microRNA in the subject as compared to the base level is indicative of cancer or pre-cancer.

BRIEF DESCRIPTION OF THE DRAWINGS

FIG. 12 shows the sequence of primers used for the qMS-PCR (SEQ ID NOs. 1-10) and the sequences of the genomic loci encoding miR124-1, 124-2, 124-3, 137 and 9-1 (SEQ ID NOs. 11-15).

DETAILED DESCRIPTION

Figure 1:
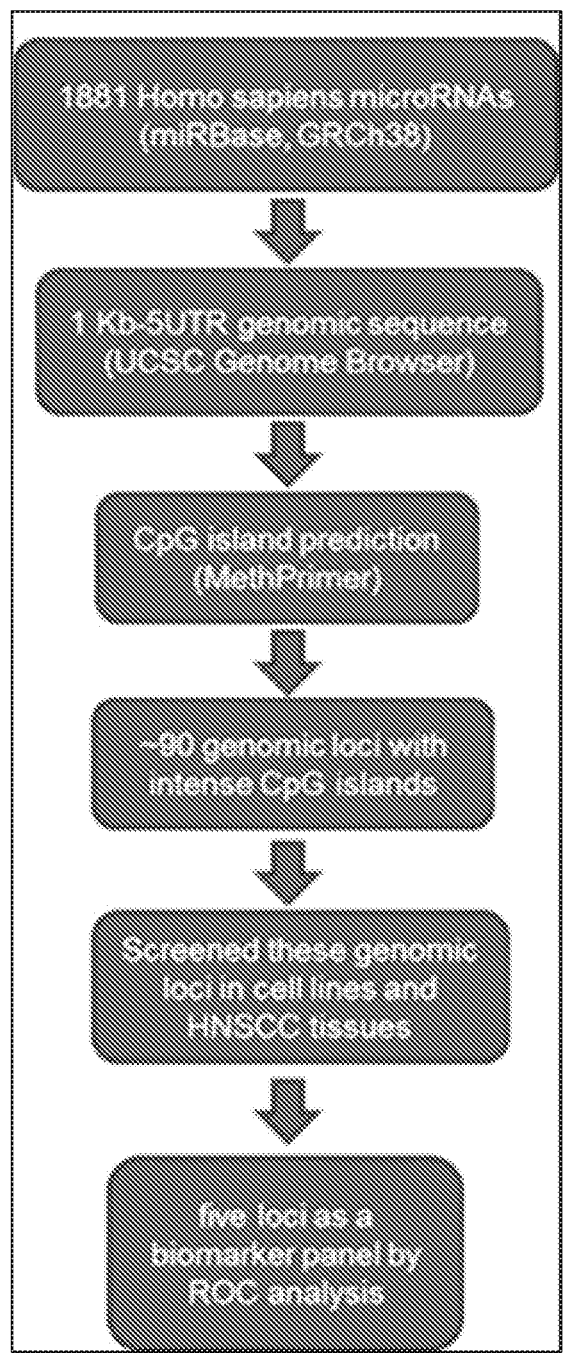
FIG. 1 shows flow chart of genome wide search for mgmiRs in HNSCC.
Figure 2:
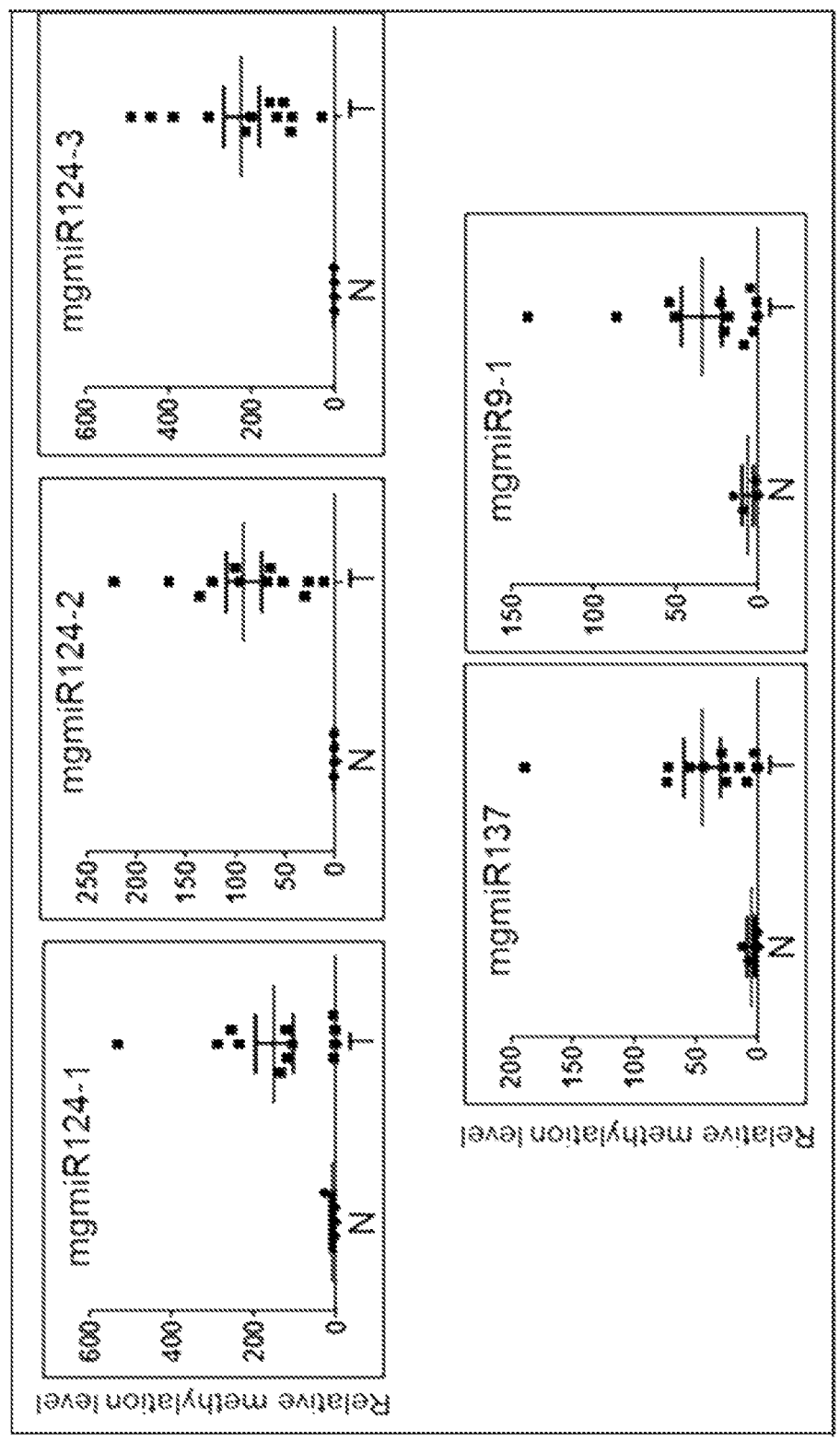
FIG. 2 shows relative methylation level of the mgmiRs examined by qMS-PCR in 12 HNSCC cell lines (T) and 4 head and neck control cell lines (N).

The discovery of microRNA (miRNA) was a major event in molecular biology. See Lee et al. (1993). miRNAs are non-coding RNAs that are approximately 18-25 nucleotides in length. These molecules appear to be evolutionary conserved and instead of being translated into proteins, their main role is in gene regulation. Over the past twenty years, multiple studies have demonstrated that miRNAs serve important roles and affect fundamental cell processes, such as cellular development, differentiation, proliferation, survival and death. Ambros et al. (2004).

Over 1000 miRNAs have been discovered in the human genome with research demonstrating that one miRNA family on average affects approximately ~500 genes. See e.g., Lewis et al. (2003); Krek et al. (2005), Betel et al. (2008), and Friedman et al. (2009). Because of this prominent regulatory role on cellular genomics, researchers have investigated whether altered miRNAs play a role in tumorigenesis. Interestingly, studies have shown that miRNA may play a role in tumorigenesis in human neoplasia having distinctive miRNA expression signatures. Furthermore, miRNAs appear to have both tumor suppressor and oncogenic roles in tumorigenesis. With this discovery, extensive research has been focused on the possibility of miRNA as a potential target for cancer diagnosis and therapy. See e.g., Garzon et al. (2010).

Another significant development in genetic research has been the increased understanding of epigenetics. Epigenetics is the study of heritable changes in gene activity that are not caused by alterations in the actual DNA. Probably the best known and scientifically established epigenetic process is DNA methylation. The addition of a methyl group to the DNA promoter region especially of the CpG-rich sequences of a specific gene has been shown to be a strong repressor of transcription equivalent to an actual mutation or deletion of the gene. In the last 15 years or so, epigenetics has been shown to play a significant role in the development of cancer. Specifically, hypermethylation of critical tumor suppressor genes has been revealed in many cancers, including HNSCC. See Worsham et al. (2013).

The majority of HNSCC affects the mucosal surface of the upper aerodigestive tract, which also includes esophageal cancer and lung cancer. To date, it still remains unanswered whether specific epigenetic changes could be used as a diagnostic tool for HNSCC.

The present disclosure provides a method of using qMS-PCR to examine the methylation level of genomic loci encoding microRNAs (mgmiRs") in HNSCC. After genome-wide searching for CpG islands in the 1KB 5UTRs of 1881microRNA and screening more than fifty genomic loci encoding microRNA markers, miR124 (124-1, 124-2 and 124-3), miR137 and miR9 (9-1), proved to be the best markers for detection of HNSCC. This set of 5 markers which, when used as a panel in combination, detected HNSCC with 100% specificity and 90% sensitivity. These markers may act at different sites or via different mechanisms.

In one embodiment, the relative methylation level within the adjacent mucosa group was significantly lower than that of the tumor group. However, compared to the normal control group there was a higher relative methylation level in the adjacent mucosa, and this was statistically significant. This finding has early diagnostic significance as our panel has the potential to detect pre-malignant changes in surrounding tissue. A study by Roh et al in 2011 examined the feasibility of tissue imprinting and the use of qMS-PCR to assess the methylation patterns of 4 genes in the margins of head and neck cancer specimens. Our study examined the presence of microRNA methylation level in adjacent mucosa, and also found that this is a technique with adequate sensitivity and specificity to detect cancer in tissue that appears grossly normal surrounding a tumor.

In another embodiment, as with any test that has an objective numeric outcome, a threshold level may be set above which the test is considered "positive." All of the markers, with the exception of the mgmiR9-1, showed certain level of baseline methylation expression within the cancer-free control group. In order to define and develop our panel for potential clinical use, a threshold methylation level was chosen for each marker. To this end, a weighted Youden Index was used to derive the optimal cutoff for each mgmiR marker.

The term "cancer" refers to a group of diseases involving abnormal cell growth that may invade or spread to other parts of the body. The term "pre-cancer" refers to a state in which a malignant tumor, or hyperplasia/dysplasia may have formed but have not started to or gained the capability to invade or spread to other parts of the body.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1 Identification of DNA Methylation at Genomic Loci Encoding miR124, miR137 and miR9 in HNSCC Cell Lines To identify methylated genomic loci encoding miRNAs in HNSCC, the UCSC genome browser was used to obtain 1Kb genomic sequences of 5'-UTRs of 1881 Homo sapiens primary (Pri-) miRNAs in the miRBase database. The CpG island prediction software (MethPrimer) was then utilized to identify ~90 genomic loci with CpG islands (defined as island size >200 bp, GC content>50%, observed/expectation>0.6). By designing methylation specific primers and running quantitative methylation specific PCR (qMS-PCR), we screened these genomic loci and found five loci encoding pri-miR, i.e. 124-1, 124-2, 124-3, 137 and 9-1 that had increased methylation in human HNSCC cell lines compared to normal head and neck cell lines (FIG. 1 and Table 1). These methylated genomic loci encoding miRNAs were referred to as mgmiRs. As shown in Table 1, we examined relative methylation levels in 12 HNSCC cell lines including cell lines derived from age ranging from 22 to 70 years old, both male and female, HPV positive and negative HNSCCs, an HNSCC from Fanconi anemia patient and different anatomic sites of head and neck region. Four head and neck normal cell lines were included as controls.

TABLE 1

Relative methylation levels of mgmiRs in human HNSCC cell lines and normal head and neck cell lines

| cell lines | Sources | mgmiR124-1 | mgmiR124-2 | mgmiR124-3 | mgmiR137 | mgmiR9-1 |
| --- | --- | --- | --- | --- | --- | --- |
| UMSCC10A | LSCC | 5.31 | 26.77 | 102.74 | 8.34 | 2.5 |
| UMSCC10B | Ln mets | 236.39 | 64.39 | 105.37 | 55.91 | 0.61 |
| UMSCC22A | HPSCC | 0 | 52.55 | 215.09 | 25.45 | 20.54 |
| UMSCC22B | Ln mets | 287.33 | 100.3 | 304.43 | 28.93 | 50.57 |
| UMSCC2 | OSCC rec. | 104.26 | 96.03 | 155.81 | 14.72 | 86.33 |
| UMSCC47 | OSCC, HPV+ | 254.29 | 123.93 | 201.95 | 0 | 18.01 |
| FaDu | PSCC | 532.97 | 223 | 388.9 | 188.67 | 140.34 |
| Cal27 | OSCC | 117.86 | 135.53 | 442.41 | 43.79 | 53.87 |
| SCC9 | OSCC | 0 | 10.85 | 123.72 | 2.54 | 4.58 |
| SCC25 | OSCC | 3.7 | 68.46 | 31.01 | 73.64 | 0.63 |
| Detroit562 | PSCC | 133.43 | 29.92 | 140.32 | 27.3 | 8.29 |
| Vu1365 | OSCC, FA-A | 120.45 | 167.24 | 490.79 | 72.52 | 22.72 |
| OKF6 | Keratinocytes | 1 | 1 | 1 | 0 | 1 |
| NHEK | Keratinocytes | 0.28 | 0.87 | 0.31 | 0 | 0 |
| NIKS | Keratinocytes | 0.3 | 0.22 | 0.47 | 12.54 | 8.96 |
| Hacat | Keratinocytes | 26.53 | 0.81 | 0 | 7.79 | 14.52 |

LSCC: laryngeal SCC,
Ln mets: lymph node metastasis,
HPSCC: hypopharynx SCC,
OSCC rec.: oral SCC recurrence,
HPV: human papilloma virus,
PSCC: pharynx SCC,
FA-A: fanconi anemia A

Example 2 Development of a Diagnostic Panel of mgmiR Biomarkers for Head and Neck Cancer in Patient Cohort 1

This study was conducted on human HNSCC surgical samples in compliance with the Institutional Review Board (IRB) approved protocols from relevant institutions. A total of 64 different tissue specimens were used (n=64). Table 2 shows the breakdown of the study population. Thirty samples were HNSCC specimens from the time of surgical resection (n=30 tumor specimens). This group constituted our "Tumor" group. 26 of these patients also had grossly normal tissue that was collected at the time of surgery from an area adjacent to the primary tumor. These specimens comprised our "adjacent mucosa" group (n=26), and represent grossly normal appearing tissue with hyperplasia/dysplasia under microscope from patients with known head and neck cancer. Oral tissues from 8 healthy patients with no history of malignancy were used as normal control population (n=8). (Table 2).

TABLE 2

Study Population Groups in patient's cohort 1.

Tissue Sample Groups

| Tumor (T) | n = 30 |
|---|---|
| Adjacent Mucosa (M) | n = 26 |
| Normal Controls (N) | n = 8 |

All fresh tumor bank tissues were stored in liquid nitrogen until the time of DNA extraction. Genomic DNA was extracted from each tissue sample using the DNeasy Blood & Tissue kit (Qiagen), and was quantitated using the Nanovue spectrophotometer (GE Healthcare). The genomic DNA was then treated with bisulfate using the EZ DNA Methylation-Gold kit (Zymo) and following the manufacture's instruction.

The bisulfate converted DNAs were subjected to the SYBR-green based Quantitative Methylation Specific PCR (qMS-PCR) for the five mgmiRmarkers. For each individual marker, the qMS-PCR protocol was optimized prior to beginning running samples, in order to identify the proper annealing temperature and maximize the results to obtain a typical sigmoid result curve. Melting curves together with gel running were applied to determine the specificity of each marker. Variables adjusted included the temperature, number of cycles, and length of each cycle. Beta-actin was used as an internal control. qMS-PCR was running in triplicates on the CFX connect™ real time detection system (Biorad). Each plate included patient DNA samples, positive control (in vitro methylated DNA), negative control (DNA from a known unmethylated cell line), and water blanks. For each sample within each marker, a relative methylation level was calculated using the difference in Ct values by the standard $2^{-\Delta\Delta Ct}$ method.

Statistical Analysis of qMS-PCR results. To allow for all qMS-PCR results to be compared, one control patient was set up as a negative control and the methylation level was arbitrarily defined as one for this patient to calibrate the results for all other patients. For each qMS-PCR experiment, three data points ($\Delta\Delta CT$ value, +SD, −SD) were generated from each sample's triplicate on each qMS-PCR experiment.

Receiver operating characteristic (ROC) curve was used to evaluate the performance of each biomarker. A ROC curve is a graphical plot which illustrates the performance of a binary classifier system (in this project, the biomarker of interest) as its discrimination threshold (the cutpoint to be identified) is varying. The area under curve (AUC) for each ROC curve plotted is reported here. A greater AUC value generally indicates a better-performing biomarker. A perfect diagnostic test would have an AUC value of 1.

Youden's Index was used to derive the cutpoint. The optimal cutpoint should maximize Youden's Index. Unweighted Youden's index is defined J=sensitivity+specificity −1. Weighted Youden's Index is defined J=w*sensitivity+(1-w)*specificity, where w represents a given weight. Naturally, unweighted Youden's puts equal emphasis on sensitivity and specificity. To enhance the specificity, we assigned a higher weight to specificity than sensitivity. The optimal cut-points that maximize the two Youden's were identified, respectively. For the weighted Youden's, a 20% weight to sensitivity and an 80% weight to specificity (in an unweighted Youden sensitivity and specificity can be considered as both having 50% weight) were arbitrarily assigned.

A two-tailed t-test with unequal variance was then used to calculate the significance of differences among the normal control, adjacent mucosa, and tumor groups. Significance was tested for each marker individually, and for the panel as a whole. p<0.05 is considered statistically significant.

The relative methylation levels of each methylated microRNA marker as measured by qMS-PCR are shown below and are also summarized in Table 3.

TABLE 3

Percentage of positive methylated microRNA cases in tumor tissues, and adjacent mucosa from HNSCC patients, and normal tissues from control patients

Figure 3:
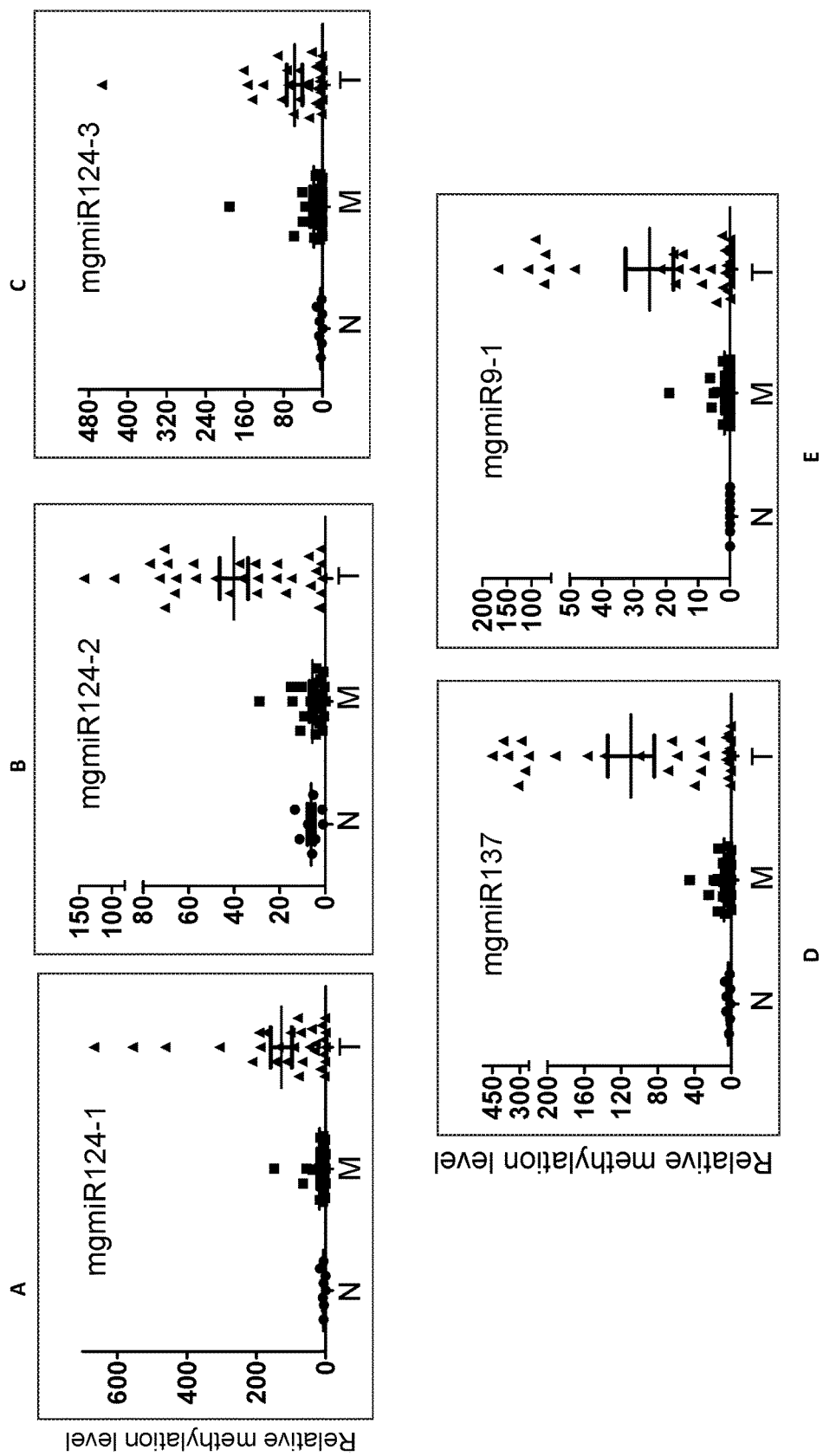
FIG. 3 shows relative methylation level measured by individual mgmiR biomarkers in patient cohort 1. N-normal buccal mucosa from a cancer-free individual, M-adjacent mucosa from an HNSCC patient, T-tumor tissue from an HNSCC patient.

| | Tumor | Adjacent Mucosa | Normal Mucosa |
|---|---|---|---|
| mgmiR124-1 | 70% (21/30) | 15.4% (4/26) | 0% (0/8) |
| mgmiR124-2 | 70% (21/30) | 3.8% (1/26) | 0% (0/8) |
| mgmiR124-3 | 63.3% (19/30) | 23.1% (6/26) | 0% (0/8) |
| mgmiR137 | 60% (18/30) | 3.8% (1/26) | 0% (0/8) |
| mgmiR9-1 | 56.7% (17/30) | 11.5% (3/26) | 0% (0/8) |
| combination | 90% (27/30) | 38.5% (10/26) | 0% (0/8) | mgmiR 124-1: The relative methylation level of mgmiR124-1 is 6.60 within the normal control population. Within the tumor group the mean relative methylation level was 128.08 (SE 30.62), and within the adjacent mucosa group the mean relative methylation level was 18.14 (SE 6.13) (FIG. 3A).

mgmiR 124-2: The relative methylation level of mgmiR124-2 is 6.29 within the normal control population. Within the tumor group the mean relative methylation level was 40.21 (SE 6.24), and within the adjacent mucosa group the mean relative methylation level was 5.73 (SE 1.23) (FIG. 3B).

mgmiR124-3: The relative methylation level of mgmiR124-3 is 4.37 within the normal control population. Within the tumor group the mean relative methylation level was 57.66 (SE 16.29), and within the adjacent mucosa group the mean relative methylation level was 18.22 (SE 7.57) (FIG. 3C).

mgmiR 137: The relative methylation level of mgmiR137 is 3.19 within the normal control population. Within the tumor group the mean relative methylation level was 109.30 (SE 25.31), and within the adjacent mucosa group the mean relative methylation level was 8.08 (SE 0.82) (FIG. 3D).

mgmiR 9-1: mgmiR 9-1 was the only marker in the group that showed no baseline methylation level within the control population, and methylation level was found only in cancer specimens. Within the tumor group the mean relative methylation level was 25.14 (Standard Error (SE) 7.44), and within the adjacent mucosa group the mean relative methylation level was 1.80 (SE 0.79) (FIG. 3E).

Combination of 5 biomarkers: When comparing the relative methylation level of all 5 mgmiR markers as a whole, the relative methylation signal was 4.09 for the normal control population, and 72.08 for the tumor population. This difference was statistically significant (p<0.001). The relative methylation level in the adjacent mucosa was 10.39. When compared to the methylation level of the normal controls, this difference also demonstrated statistical significance (p=0.005).

After the relative methylation level of the five mgmiR biomarkers had been measured, a receiver operating characteristic curve and a weighted Youden's Index to derive the cut-off value were used. For more details, refer to the Material and Methods section above. These calculations were done from the qPCR results for each marker and each sample.

Using these 5 markers in a combined panel, these results showed 90% sensitivity and 100% specificity in the detection of squamous cell carcinoma within 30 tumor specimens (Tables 3 and 4). Interestingly, within the adjacent mucosa specimens, the sensitivity was 38.5% and the specificity was 100% for the detection of squamous cell carcinoma (Tables 3 and 4).

TABLE 4

Sensitivity and specificity in HNSCC tissues and control tissues from patient cohort 1

| Tested Biomarker | Area under the Curve | Sensitivity at Maximum Weighted Youden's Index | Specificity at Maximum Weighted Youden's Index | Maximum Weighted Youden's Index | Opimtimal Cutoff Based on Maximum Weighted Youden's Index |
|---|---|---|---|---|---|
| mgmiR124-1 | 0.7853 | 70.00% | 100% | 0.8898 | −6.07755 |
| mgmiR124-2 | 0.8186 | 70.00% | 100% | 0.92 | −4.8919 |
| mgmiR123-3 | 0.7333 | 63.30% | 100% | 0.84314 | −5.91568 |
| mgmiR137 | 0.7304 | 60.00% | 100% | 0.89647 | −4.89068 |
| mgmiR9-1 | 0.802 | 56.70% | 100% | 0.88 | −2.54753 |
| combine | | 90% | 100% | | |

Example 3 Identification and use of Saliva mgmiRs as Novel Non-invasive Biomarkers for HNSCC Patients Cohort 2

This study was conducted on human HNSCC tissue samples as well as saliva samples from patients. The study was approved by the Institutional Review Board (IRB) and patient's consent was obtained prior to use of sample. Tissue and/or saliva samples were collected from 36 patients as cohort.

Tissue and saliva samples were either labeled as subject (tumor) or control. The subject group consisted of patients that had a diagnosis concerning for HNSCC. Tissue and saliva was obtained from 24 HNSCC patients. Tissue from these patients was confirmed to be HNSCC tissue based on clinical exam and/or previous biopsies. Tumor tissue was obtained in the operating room when patients underwent either surgical resection or biopsy. Saliva was gathered from patients before they underwent surgical resection.

The control group consisted of patients who are cancer-free. Tissue and saliva was obtained from 12 control patients undergoing tonsillectomy. Indications for tonsillectomy were either for obstructive sleep apnea and/or chronic tonsillitis. Tissue was collected in the operating room and consisted of normal mucosa from the anterior tonsillar pillar and/or tonsil tissue. Saliva was gathered from patients before they underwent surgical resection. Saliva was also collected from five disease-free healthy volunteers.

Demographic information of patients in this study was gathered as well as human papilloma virus (HPV) status, use of tobacco products and alcohol, any previous chemotherapy and/or radiation, history of cancer, and family history of cancer. In the subject group information regarding the clinical stage and grade of the tumor tissue as well as pathologic features and molecular markers was also reviewed and compiled once pathology was finalized for the tissue samples. All information collected was placed in an encrypted database and samples were listed without patient identifiers.

After harvesting, tissue was immediately taken to the laboratory where it was frozen and stored in liquid Nitrogen until later DNA extraction. 30 minutes before saliva collection, patients/volunteers need to stop taking food, drinking, chewing gums and smoking. By the time of saliva collection, patients rinsed their mouths with normal saline for two times with interval of 2 minutes. Patients/volunteers were then instructed to spit their saliva into a Falcon 50 ml collection tubes for 2-3 times with an interval of 2 minutes for 2-3 times. approximately, 4-5 mL of saliva was obtained from the majority of patients with some samples has limited volume due to xerostomia. Once collected, samples were taken to the laboratory, where it was stored in a −20 degree Celsius freezer.

Isolation of genomic DNAs and bisulfite conversion. Genomic DNA was extracted from each tissue sample using the DNeasy Blood & Tissue kit (Qiagen) according to the manufacture's instruction. For saliva genomic DNA extraction, the frozen saliva samples were melted slowly at room temperature, and were added additional 5 ml saliva preparation buffer to the each saliva sample for stabilization of genomic DNA at room temperature. The saliva samples were then centrifuged with 5000 rpm for 15 minutes. Five different genomic DNA extraction kits were tested. The QiaAmp DNA mini kit gave the best yield and quality of genomic DNA from saliva. The genomic DNA was then quantitated using the Nanovue spectrophotometer (GE Healthcare). The genomic DNA was then treated with bisulfite using the EZ DNA Methylation-Gold kit (Zymo) and following the manufacture's instruction.

Quantitative Methylation Specific PCR (qMS-PCR). The bisulfate converted DNAs were subjected to the SYBR-green based qMS-PCR for the five mgmiR markers (primer sequences for the qMS-PCR are as shown in SEQ ID NOs. 1-10). For each individual marker, the qMS-PCR protocol was optimized prior to beginning running samples, in order to identify the proper annealing temperature and maximize the results to obtain a typical sigmoid result curve. Melting curves together with gel running were applied to determine the specificity of each marker. qMS-PCR was running using SYBR green mix (Biorad) under the following thermo condition: 95 C 3 min, 95 C 30 sec, 55-60C 30 sec for 40 cycles. Beta-actin was used as an internal control. qMS-PCR was running in triplicates on the CFX connect™ real time detection system (Biorad). For each sample within each marker, a relative methylation level was calculated using the difference in Ct values by the standard $2^{-\Delta\Delta Ct}$ method.

Statistical Analysis of qMS-PCR results. To allow for all qMS-PCR results to be compared, one control patient was set up as a negative control and the methylation level was arbitrarily defined as one for this patient to calibrate the results for all other patients. For each qMS-PCR experiment, three data points (ΔΔCT value, +SD, −SD) were generated from each sample's quadruplicate on each qMS-PCR experiment.

Receiver operating characteristic (ROC) curve was used to evaluate the performance of each biomarker. A ROC curve is a graphical plot which illustrates the performance of a binary classifier system (in this project, the biomarker of interest) as its discrimination threshold (the cutpoint to be identified) is varying. The area under curve (AUC) for each ROC curve plotted is reported. A greater AUC value generally indicates a better-performing biomarker. A perfect diagnostic test would have an AUC value of 1.

Youden's Index was used to derive the cutpoint. The optimal cutpoint should maximize Youden's Index. Unweighted Youden's index is defined J=sensitivity+specificity−1. Weighted Youden's Index is defined J=w*sensitivity+(1−w)*specificity, where w represents a given weight. Naturally, unweighted Youden's puts equal emphasis on sensitivity and specificity. To enhance the specificity, a higher weight was assigned to specificity than sensitivity. The optimal cut-points that maximize the two Youden's were then identified, respectively. For the weighted Youden's, a 20% weight was arbitrarily assigned to sensitivity and an 80% weight to specificity (in an unweighted Youden sensitivity and specificity can be considered as both having 50% weight).

A two-tailed t-test with unequal variance was then used to calculate the significance of differences among the normal control, adjacent mucosa, and tumor groups. Significance was tested for each marker individually, and for the panel as a whole. $p<0.05$ is considered statistically significant.

Figure 4:
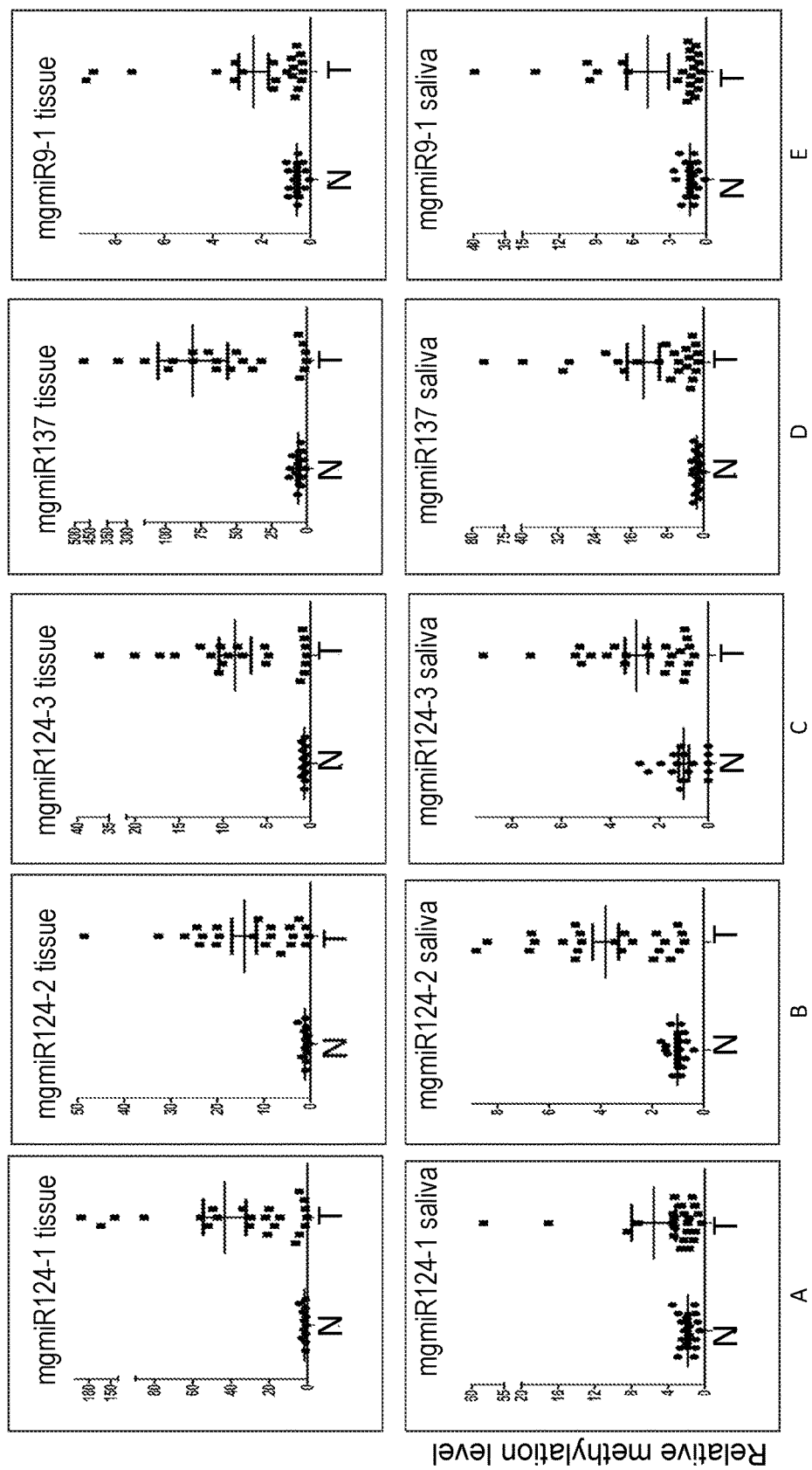
FIG. 4A shows qMS-PCR results that reveal the overall relative methylation level of both the control and subject samples as well as the methylation level of each patient's saliva (lower) and tumor sample (upper) for marker mgmiR124-1.
FIG. 4B shows qMS-PCR results that reveal the overall relative methylation level of both the control and subject samples as well as the methylation level of each patient's saliva (lower) and tumor sample (upper) for marker mgmiR124-2.
FIG. 4C shows qMS-PCR results that reveal the overall relative methylation level of both the control and subject samples as well as the methylation level of each patient's saliva (lower) and tumor sample (upper) for marker mgmiR124-3.
FIG. 4D shows qMS-PCR results that reveal the overall relative methylation level of both the control and subject samples as well as the methylation level of each patient's saliva (lower) and tumor sample (upper) for marker mgmiR137.
FIG. 4E shows qMS-PCR results that reveal the overall relative methylation level of both the control and subject samples as well as the methylation level of each patient's saliva (lower) and tumor sample (upper) for marker mgmiR9-1.

The following five mgmiRs were analyzed: mgmiR124-1, 2, 3, mgmiR137, and mgmiR9-1. Shown in FIG. 4 (panels A-E) are qMS-PCR results that reveal the overall relative methylation level of both the control and subject samples as well as the methylation level of each patient's saliva and tumor sample for each marker. The HeatMap of comparison of these mgmiR biomarkers was obtained and sensitivity and specificity were calculated for each miRNA marker in the saliva and the tissue samples using Youden's index. Also, overall sensitivity and specificity was determined when all miRNA markers were used together. These results are listed in Table 5 and Table 6.

TABLE 5

Sensitivity and specificity in HNSCC patients' tissues

| Tested Biomarker | Area under the Curve | Sensitivity at Maximum Weighted Youden's Index | Specificity at Maximum Weighted Youden's Index | Maximum Weighted Youden's Index | Optimal Cutoff Based on Maximum Weighted Youden's Index |
|---|---|---|---|---|---|
| mgmiR124-1 | 0.8333 | 68.2% | 100% | 0.93636 | −1.50375 |
| mgmiR124-2 | 0.7955 | 63.6% | 100% | 0.92727 | −0.43000 |
| mgmiR124-3 | 0.8258 | 68.2% | 100% | 0.93636 | 0.35250 |
| mgmiR137 | 0.7803 | 68.2% | 100% | 0.93636 | −2.54667 |
| mgmiR9-1 | 0.6925 | 19.0% | 100% | 0.83810 | −0.48317 |
| Combine | | 90.5% | 100% | | |

TABLE 6

Sensitivity and specificity in HNSCC patients' saliva

| Tested Biomarker | Area under the Curve | Sensitivity at Maximum Weighted Youden's Index | Specificity at Maximum Weighted Youden's Index | Maximum Weighted Youden's Index | Optimal Cutoff Based on Maximum Weighted Youden's Index |
|---|---|---|---|---|---|
| mgmiR124-1 | 0.5602 | 0.08333 | 100% | 0.81667 | −1.85588 |
| mgmiR124-2 | 0.8102 | 0.66667 | 100% | 0.93333 | −0.54500 |
| mgmiR124-3 | 0.7500 | 0.33333 | 100% | 0.86667 | 0.10375 |
| mgmiR137 | 0.7708 | 0.45833 | 100% | 0.89167 | −1.62375 |
| mgmiR9-1 | 0.5185 | 0.08333 | 100% | 0.81667 | −1.28667 |
| Combine | | 81% | 100% | | |

Figure 5:
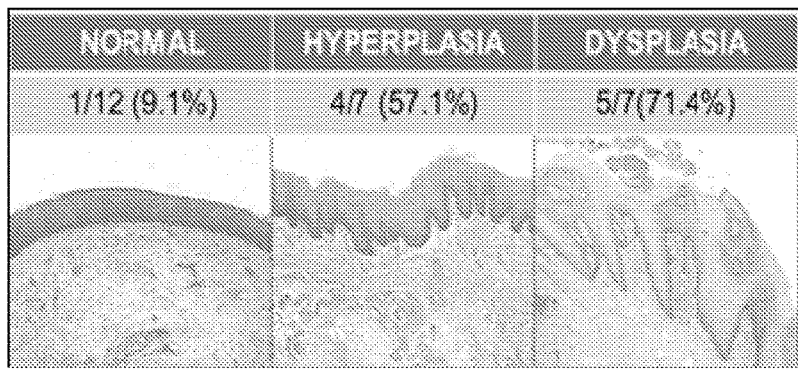
FIG. 5 shows positive cases examined by the mgmiRs in adjacent mucosa of HNSCC.

Example 4 Biomarker as a Means for Assessing HNSCC Treatment Effects and for Post-treatment Monitoring The two patient cohorts were combined, and a total of 51 HNSCC tissues were assessed, including 23 from the oral cavity, 9 from the oropharynx, 2 from the hypopharynx, 14 from the larynx, and 3 cutaneous HNSCC cases. The 21 saliva samples from patient cohort 2 included 10 oral cavity, 5 oropharynx, 1 hypopharynx, and 5 larynx HNSCC cases. No significant differences were observed between positive cases and anatomic sites or T stage. As shown in Table 7, 88% of positive cases were detected from tissues and 75% of positive cases from saliva samples when the tumor was at T1 stage. These results suggested that these mgmiRs can be used as early detection markers when tumors are still small. The same cut-off points were used to dichotomize the adjacent mucosa group in patient cohort 1 (FIG. 3). 10 (38.5%) positive cases were identified among the 26 adjacent mucosa samples. As shown in FIG. 5, histological examination showed 5 (71.4%) positive cases among 7 dysplasia cases, and 4 (57.1%) positive cases among 7 hyperplasia cases. This percentage was higher than one (9.1%) positive case in the 12 normal adjacent mucosa samples, suggesting the possibility of using the five mgmiR biomarkers for early detection of HNSCC.

TABLE 7 positive cases examined by the five mgmiRs

| | tissue | saliva |
|---|---|---|
| T1 | 7/8 (88%) | 3/4 (75%) |
| T2 | 14/17 (82%) | 4/5 (80%) |
| T3 | 10/11 (91%) | 5/6 (83%) |
| T4 | 14/15 (93%) | 5/6 (83%) |

Figure 6:
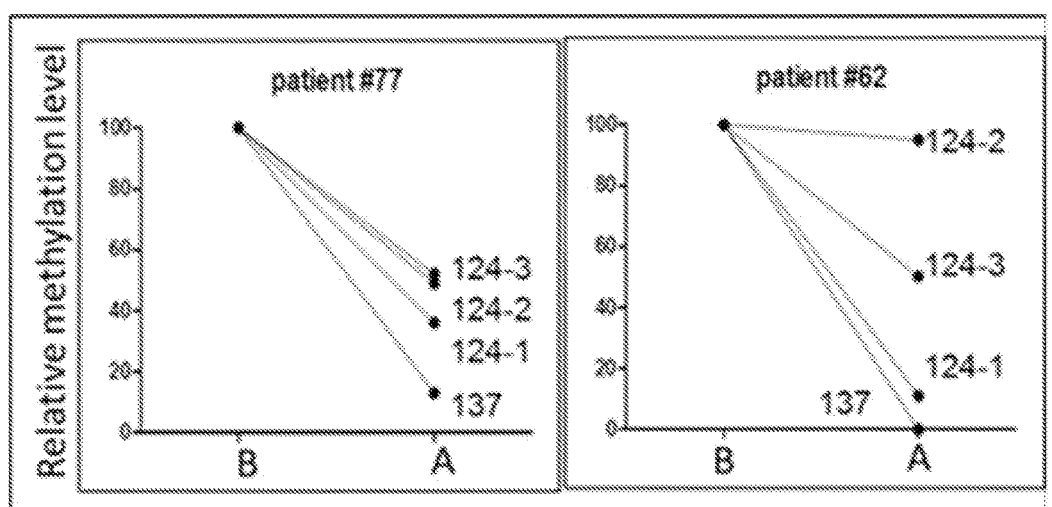
FIG. 6 shows decrease of methylation level ofmg-miR124s andmg-miR137) in patient's saliva DNA after surgical removal of tumor. B (before surgery), A (after surgery).

In addition, as shown in FIG. 6, methylation levels of the mgmiR124-1, 124-2, 124-3 and 137 in patients' saliva DNA were significantly reduced in three HNSCC patients after surgical removal of their tumors. Thus, the methylation levels of the mgmiRs in patients' saliva DNA correlate with the tumor burden. This result supports the feasibility of using the mgmiRs with patients' saliva DNA for HNSCC surveillance after surgery.

One purpose of this study was to investigate whether patients with HNSCC had higher rates of methylation in five genomic loci for specific miRNAs (miR124-1, 124-2, 124-3, 137, 9-1) that may have tumor suppressor roles. It was hypothesized that this difference could be detected not only in tissue samples, but also from the patient's saliva.

The disclosed data revealed a disparity in methylation between the subject and control samples. Comparison of all control and subject tissue samples demonstrated a significant difference in methylation for all five mgmiRNAs. Similarly, when control and tissue saliva samples were compiled and compared, higher levels of methylation for all five mgmiR-NAs were observed, with 124-1, 124-2, and 137 showing a significant difference between control and subject samples. The higher level of methylation in the subject population may highlight a downregulation of their corresponding encoded miRNAs and underline their possible suppressor role in tumorigenesis.

Breaking the methylation data further down into each individual control and subject sample, further illustrated this trend that subject samples had higher levels of methylation than the control samples. Sensitivity and specificity values demonstrated that in the saliva samples the mgmiR124-2 was the most sensitive miRNA marker followed by 137, 124-3, 9-1, and 124-1. In tissue samples, mgmiR124-2 was also the most sensitive miRNA marker followed by 137, 124-1, 124-3, and 9-1. The tissue samples were overall more sensitive than the saliva samples with all five miRNA markers having a greater than 50% sensitivity in the tissue samples. The specificity of the mgmiR markers was much higher in both the tissue and saliva samples with all having greater than 80% specificity. Of the ten miRNA markers (5 saliva and 5 tissue), six had a specificity of 100%.

Overall, more tissue samples were positive than saliva samples. This result was not unexpected as the tissue should contain robust HNSCC DNA while the saliva samples may contain certain HNSCC DNA from tumor desquamation. Interestingly, there is strong relationship with over 80% of the saliva samples that were positive also being positive in their correlating tissue samples. The most powerful results from these data were the calculation of the overall sensitivity and specificity when all five miRNAs were used together. This result suggests potential application of these findings in a DNA microarray. When this is done, sensitivity and specificity for saliva samples are 81% and 100% and sensitivity and specificity for tissue samples are 90.5% and 100%, respectively (Tables 5 and 6).

Using clinical and pathological information, the subject samples were analyzed independently based on multiple different variables. Table 8 shows age difference between each positive and negative mgmiR biomarker.

TABLE 8

Average age of positive and negative mgmiR in HNSCC patients

|  | positive | negative |
|---|---|---|
| mgmiR137 | 62.2 years | 63.2 years |

TABLE 9 positive mgmiR cases in HNSCC patients divided by gender

|  | male | female |
|---|---|---|
| mgmiR124-1 | 82.4% (28/34) | 54.5% (6/11) |
| mgmiR124-2 | 38.2% (13/34) | 81.8% (9/11) |
| mgmiR124-3 | 58.8% (20/34) | 27.3% (3/11) |
| mgmiR137 | 65% (26/40) | 58.3% (7/12) |
| mgmiR9-1 | 40% (16/40) | 66.7% (8/12) |

TABLE 10 positive mgmiR HNSCC cases divided by location

|  | OSCC | OPSCC | LSCC |
|---|---|---|---|
| mgmiR124-1 | 70.6% (12/17) | 77.8% (7/9) | 73.3% (11/15) |
| mgmiR124-2 | 35.3% (6/17) | 66.7% (6/9) | 46.7% (7/15) |
| mgmiR124-3 | 58.8% (10/17) | 55.6% (5/9) | 53.3% (8/13) |
| mgmiR137 | 55% (11/20) | 45.5% (5/11) | 56.3% (9/16) |
| mgmiR9-1 | 60% (12/20) | 54.5% (6/11) | 25% (4/16) |

TABLE 11 positive mgmiR HNSCC cases divided by HPV status

|  | HPV+ | HPV− |
|---|---|---|
| mgmiR124-1 | 71.4% (15/21) | 79.2% (19/24) |
| mgmiR124-2 | 76.2% (16/21)* | 25% (6/24) |
| mgmiR124-3 | 52.4% (11/21) | 50% (12/24) |
| mgmiR137 | 56% (14/25) | 46.4% (13/28) |
| mgmiR9-1 | 44% (11/25) | 48.1% (13/27) |

*P < 0.01

Table 9 shows gender difference of each positive mgmiR biomarker. Table 10 shows the correlation between each mgmiR biomarker and anatomic sites. anatomic location in each positive mgmiR biomarker. Table 11 shows the correlation between each mgmiR biomarker and human papilloma virus (HPV) status.

Overall, there were no age differences between each mgmiR positive and negative cases. There were no gender differences in each mgmiR cases, except mgmiR124-2, in which the percentage of positive cases was significantly higher in women than in man. There were no significantly differences between each mgmiR biomarker and anatomic location. There was no significant correlation of the mgmiR biomarkers with HPV status, except mgmiR124-2, in which the percentage of mgmiR124-2 positive cases was significantly higher in HPV+ HNSCC patients.

In this study, specific tumor suppressor miRNAs with presumed tumor suppressor roles had higher rates of DNA methylation in patients with HNSCC as compared to control patients. This discrepancy in methylation could be detected in both patient's tissue and saliva and may underline a role of these miRNAs in tumorigenesis. Furthermore, this epigenetic difference can be used in a diagnostic test with data from this study demonstrating an overall sensitivity and specificity of over 90% in tissue and saliva samples.

Example 5 Methylation at the Genomic Loci Encoding miR124 and miR137 Silenced Expression of miR124 and miR137 in HNSCC.

Figure 7:
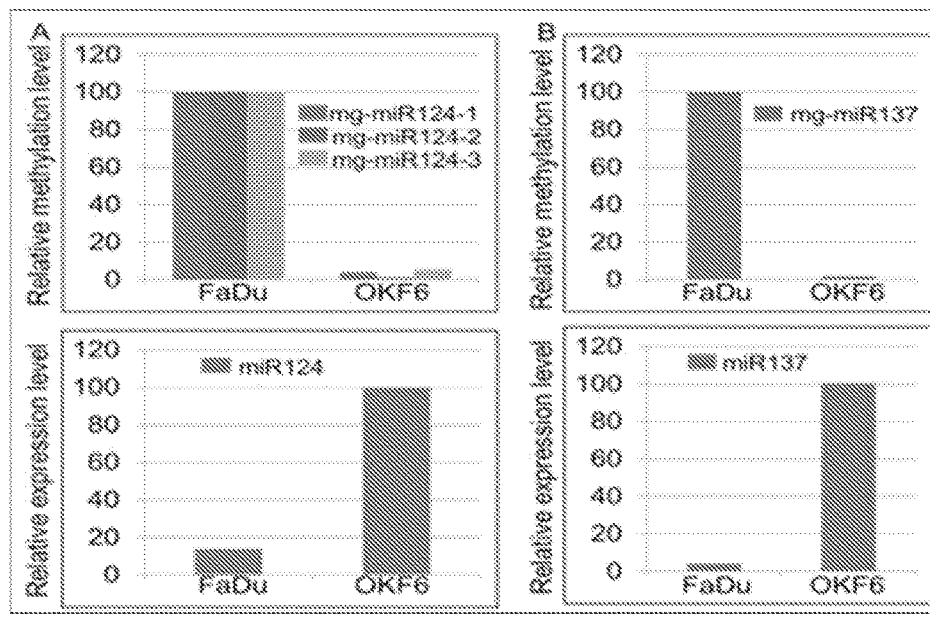
FIG. 7 shows Correlation between methylation level of the mg-miR124s (A, upper panel) or the mgmiR137 (B, upper panel) and expression level of miR124 (A, lower panel), and miR137 (B, lower panel).
Figure 8:
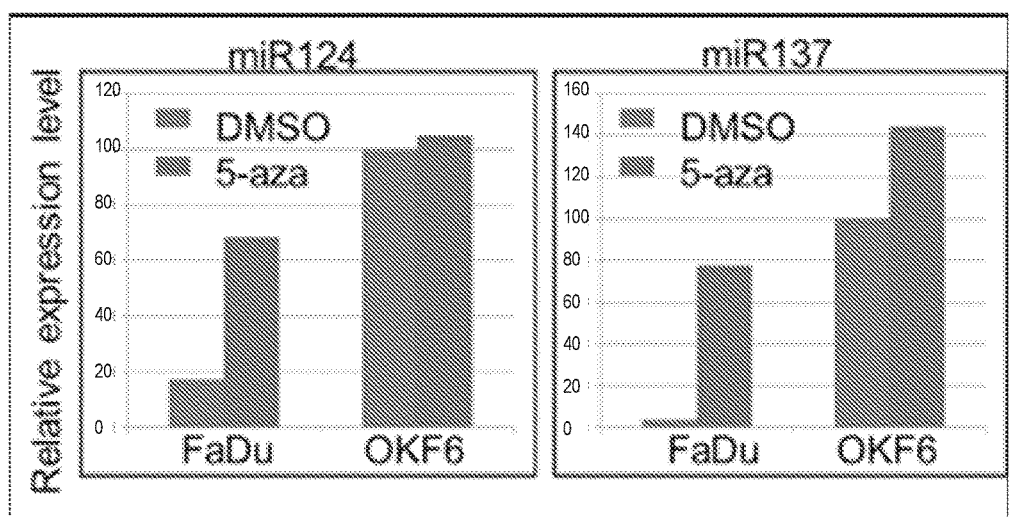
FIG. 8 shows Restoration of miR124 or miR137 expression upon 5-azacytidine (5-aza) treatment

Twelve human HNSCC cell lines and four normal human head and neck cell lines were examined to determine the correlation between DNA methylation levels and expression levels. An inverse correlation between DNA methylation levels and expression levels of miR124 and miR137 were observed. One example is shown in FIG. 7. All three genomic loci of miR124 were methylated at higher levels in the HNSCC cell line, FaDu, than in a human immortalized head and neck cell line, OKF6 (FIG. 7A, upper panel). Correspondingly, the expression level of miR124 in the FaDu cell line was lower than that in the OKF6 cell line (FIG. 7A, lower panel). A similar inverse correlation was observed between the methylation level of the mgmiR137 and the expression level of miR137 in the same cell lines. (FIG. 7B, upper panel and lower panel). The silenced expression of miR124 and miR137 due to DNA methylation was further confirmed after treatment with a demethylation reagent, 5-azacytidine (5-aza). As shown in FIG. 8, the expression levels of miR124 and miR137 were restored upon 5-aza treatment.

Figure 9:
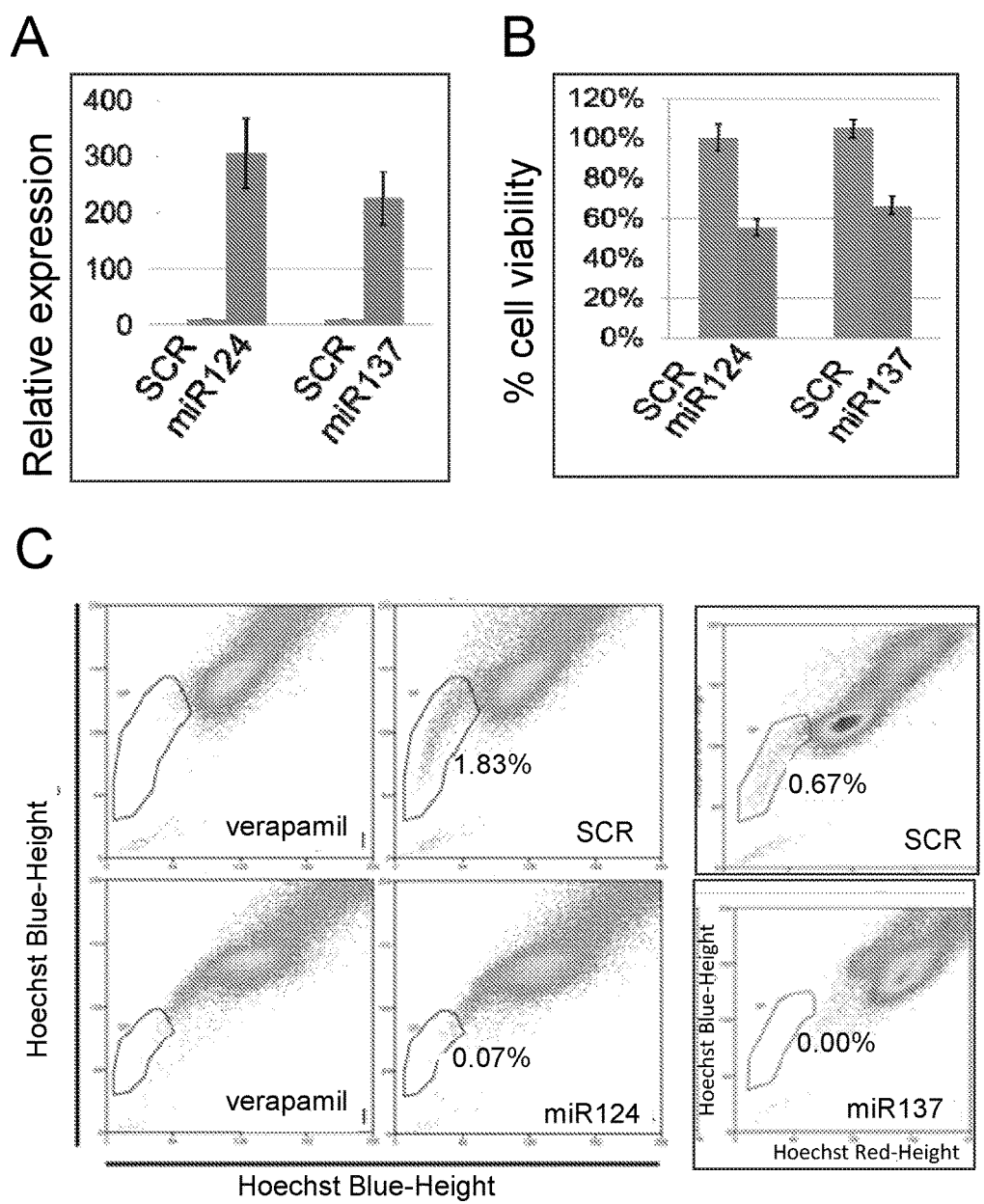
FIG. 9 shows Restoration of miR124 and miR137 mimics (A) inhibited cell proliferation (B), and SP size (C).

Example 6 Evaluated the Tumor Suppressive Functions of miR124 and miR137 in HNSCC To determine the functional role of miR124 and miR137 in HNSCC tumorigenesis, miRNA mimics of miR124 or miR137 were introduced into the FaDu cell line by transfection (FIG. 9A). A MTT cell proliferation assay was conducted 72 hours after the transfection. Cell proliferation was significantly inhibited by restoration of miR124 or miR137 expression (FIG. 9B). The effects of miR124, or miR137 in regulating tumor initiating cells (TICs) of HNSCC were further evaluated. The effects of miR124 and miR137 on TIC formation and expansion were measured using two functionally related assays: sphere forming ability and side population (SP). The sphere forming assay had been validated as being reliable for assessing the abilities of self-renewal and formation of TIC in HNSCC. In addition, the SP assay, a functional sorting method that relies on the ability of stem cells to efflux Hoechst dye, is a reliable marker for measurement of expansion of TIC in HNSCC. When miR124 or miR137 mimics were introduced into FaDu cells, the sphere forming ability of TICs was significantly disrupted and the percentage of SP was reduced. These results suggested that both miR124 and miR137 suppress the formation and expansion of TIC in HNSCC (FIG. 9C).

Example 7 Identification of Downstream Co-targets of miR124 and miR137 in HNSCC

Figure 10:
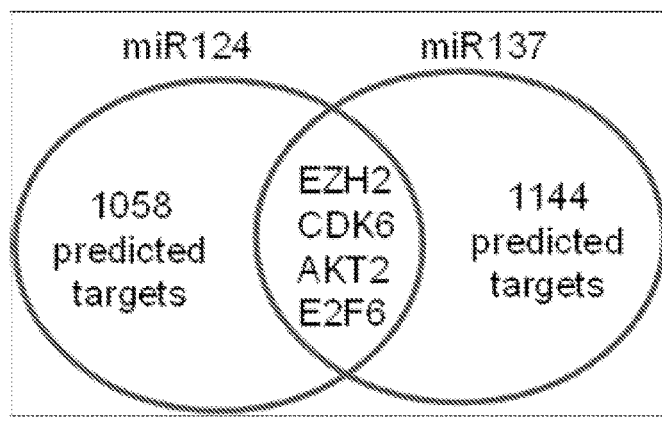
FIG. 10 shows predicted common targets for both miR124 and miR137 by TargetScan.
Figure 11:
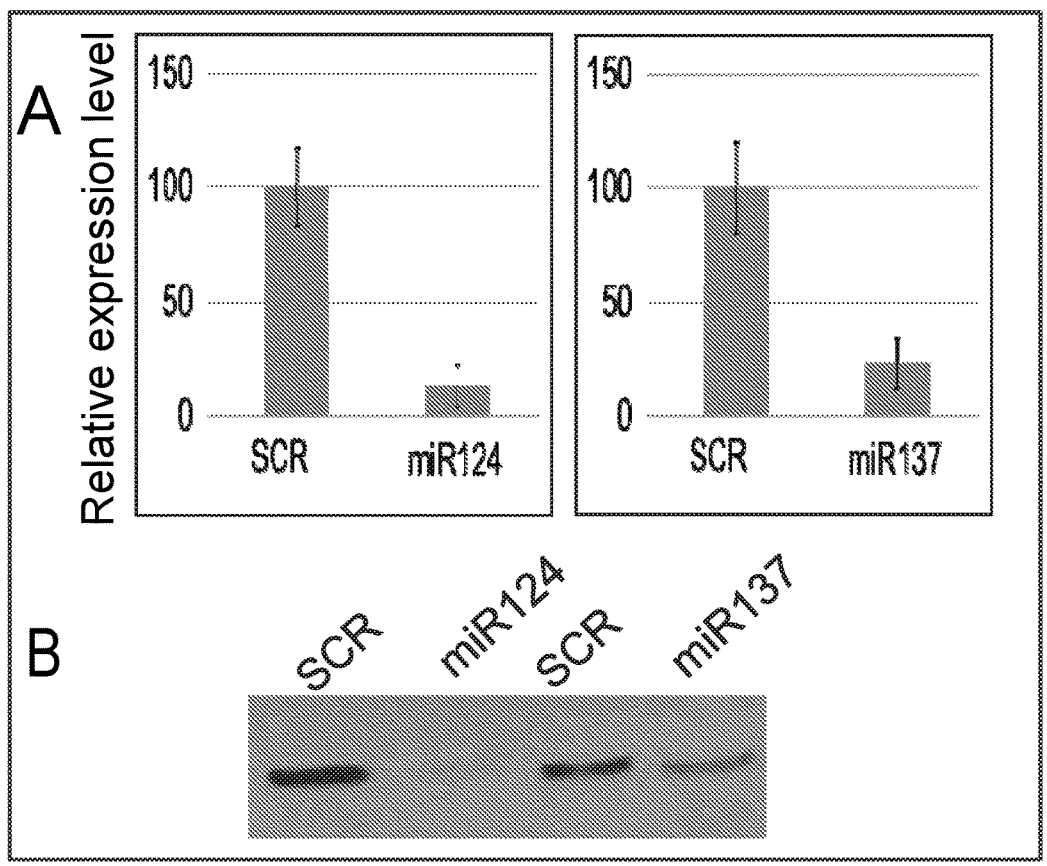
FIG. 11 shows validation of EZH2 as a downstream co-target for both miR124 and miR137. EZH2 mRNA level (A) and protein level (B) upon the restoration of miR124 and miR137 mimics.

It was hypothesized that a downstream co-target(s) for miR124 and miR137 may dominantly mediate the functions of miR124 and miR137 in HNSCC tumorigenesis. By searching the TargetScan microRNA database (version 6.2), three potential co-targets for miR124 and miR137 were found, i.e., EZH2, CDK6, AKT2, and E2F6. Each of these potential co-targets has within their 3'-UTRs >7-mer binding sites for both miR124 and miR137 conserved among vertebrates (FIG. 10). In light of its functional relevance to the maintenance of normal stem cells in keratinocytes and TICs, EZH2 was the main focus. As shown in FIG. 11, restoration of either miR124 or miR137 significantly reduced EZH2 expression at both the mRNA (A), and protein (B) levels.

REFERENCES

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of immunology, molecular biology and cell biology, which are well known in the art.

The present disclosure also incorporates by reference in their entirety techniques and methods well known in the field of molecular biology. These techniques include, but are not limited to, techniques described in the following publications.

1. Watson J D, Crick F H. Molecular structure of nucleic acids; a structure for deoxyribose nucleic acid. Nature. 1953; 171(4356):737-8.
2. Lee R C, Feinbaum R L, Ambros V. The C. elegans heterochronic gene lin-4 encodes small RNAs with antisense complementarity to lin-14. Cell. 1993; 75(5):843-54.
3. Ambros V. The functions of animal microRNAs. Nature. 2004; 431(7006):350-5.
4. Lewis, B., Shih, I., Jones-Rhoades, M., Bartel, D.& Burge, C. Prediction of mammalian microRNA targets. Cell 115,787-798 (2003).
5. Krek, D. et al. Combinatorial microRNA target predictions. Nature Genet. 37,495-500 (2005).
6. Betel, D., Wilson, M., Gabow, A., Marks, D. S. & Sander, C. The microRNA.org resource: targets and expression. Nucleic Acids Res. 36, D149-D153 (2008).
7. Friedman, R. C., Farh, K. K., Burge, C. B. & Bartel, D. P. Most mammalian mRNAs are conserved targets of microRNAs. Genome Res. 19,92-105 (2009).
8. Garzon R, Marcucci G, Croce C M. Targeting microRNAs in cancer: rationale, strategies and challenges. Nat Rev Drug Discov. 2010; 9(10):775-89.
9. Worsham M J, Ali H, Dragovic J, Schweitzer V P. Molecular characterization of head and neck cancer: how close to personalized targeted therapy?. Mol Diagn Ther. 2012; 16(4):209-22.
10. Minor J, Wang X, Zhang F, et al. Methylation of microRNA-9 is a specific and sensitive biomarker for oral and oropharyngeal squamous cell carcinomas. Oral Oncol. 2012; 48(1):73-8.
11. Boyle J O, Mao L, Brennan J A, et al. Gene mutations in saliva as molecular markers for head and neck squamous cell carcinomas. Am J Surg. 1994;168(5):429-32.
12. Worsham M J, Chen K M, Ghanem T, Stephen J K, Divine G. Epigenetic modulation of signal transduction pathways in HPV-associated HNSCC. Otolaryngol Head Neck Surg. 2013; 149(3):409-16.
13. Jemal, A.; Siegel, R.; Ward, E.; Hao, Y.; Xu, J.; Thun, M. J., Cancer statistics, 2009. *CA: a cancer journal for clinicians* 2009, 59 (4), 225-49.
14. Siegel, R.; Naishadham, D.; Jemal, A., Cancer statistics, 2013. *CA: a cancer journal for clinicians* 2013, 63 (1), 11-30.
15. Jemal, A.; Siegel, R.; Ward, E.; Hao, Y.; Xu, J.; Thun, M. J., Cancer statistics, 2009. *CA: a cancer journal for clinicians* 2009, 59 (4), 225-49.
16. Siegel, R.; Naishadham, D.; Jemal, A., Cancer statistics, 2013. *CA: a cancer journal for clinicians* 2013, 63 (1), 11-30.
17. Iorio, M. V.; Croce, C. M., MicroRNA dysregulation in cancer: diagnostics, monitoring and therapeutics. A comprehensive review. *EMBO Mol Med* 2012, 4 (3), 143-59.
18. Croce, C. M., Causes and consequences of microRNA dysregulation in cancer. *Nat Rev Genet* 2009, 10 (10), 704-14.
19. Lujambio, A.; Calin, G. A.; Villanueva, A.; Ropero, S.; Sanchez-Cespedes, M.; Blanco, D.; Montuenga, L. M.; Rossi, S.; Nicoloso, M. S.; Faller, W. J.; Gallagher, W. M.; Eccles, S. A.; Croce, C. M.; Esteller, M., A microRNA DNA methylation signature for human cancer metastasis. *Proc Natl Acad Sci USA* 2008, 105 (36), 13556-61.
20. (a) Gangaraju, V. K.; Lin, H., MicroRNAs: key regulators of stem cells. *Nat Rev Mol Cell Biol* 2009, 10 (2), 116-25; (b) Rosenfeld, N.; Aharonov, R.; Meiri, E.; Rosenwald, S.; Spector, Y.; Zepeniuk, M.; Benjamin, H.; Shabes, N.; Tabak, S.; Levy, A.; Lebanony, D.; Goren, Y.; Silberschein, E.; Targan, N.; Ben-Ari, A.; Gilad, S.; Sion-Vardy, N.; Tobar, A.; Feinmesser, M.; Kharenko, O.; Nativ, O.; Nass, D.; Perelman, M.; Yosepovich, A.; Shalmon, B.; Polak-Charcon, S.; Fridman, E.; Avniel, A.; Bentwich, I.; Bentwich, Z.; Cohen, D.; Chajut, A.; Barshack, I., MicroRNAs accurately identify cancer tissue origin. *Nat Biotechnol* 2008, 26 (4), 462-9.
21. Iorio, M. V.; Piovan, C.; Croce, C. M., Interplay between microRNAs and the epigenetic machinery: an intricate network. *Biochim Biophys Acta* 2010, 1799 (10-12), 694-701.
22. Saito, Y.; Liang, G.; Egger, G.; Friedman, J. M.; Chuang, J. C.; Coetzee, G. A.; Jones, P. A., Specific activation of microRNA-127 with downregulation of the proto-oncogene BCL6 by chromatin-modifying drugs in human cancer cells. *Cancer Cell* 2006, 9 (6), 435-43.
23. Hildebrandt, M. A.; Gu, J.; Lin, J.; Ye, Y.; Tan, W.; Tamboli, P.; Wood, C. G.; Wu, X., Hsa-miR-9 methylation status is associated with cancer development and metastatic recurrence in patients with c lear cell renal cell carcinoma. *Oncogene* 29 (42), 5724-8.

24. Saito, Y.; Jones, P. A., Epigenetic activation of tumor suppressor microRNAs in human cancer cells. *Cell Cycle* 2006, 5 (19), 2220-2.

25. Minor, J.; Wang, X.; Zhang, F.; Song, J.; Jimeno, A.; Wang, X. J.; Lu, X.; Gross, N.; Kulesz-Martin, M.; Wang, D.; Lu, S. L., Methylation of microRNA-9 is a specific and sensitive biomarker for oral and oropharyngeal squamous cell carcinomas. *Oral Oncol* 2012, 48 (1), 73-8.

26. Jones, P. A.; Baylin, S. B., The epigenomics of cancer. *Cell* 2007, 128 (4), 683-92.

27. Ha, P. K.; Califano, J. A., Promoter methylation and inactivation of tumour-suppressor genes in oral squamous-cell carcinoma. *Lancet Oncol* 2006, 7 (1), 77-82.

28. Babu, J. M.; Prathibha, R.; Jijith, V. S.; Hariharan, R.; Pillai, M. R., A miR-centric view of head and neck cancers. *Biochim Biophys Acta* 2011, 1816 (1), 67-72.

29. Roh, J. L.; Westra, W. H.; Califano, J. A.; Sidransky, D.; Koch, W. M., Tissue imprint for molecular mapping of deep surgical margins in patients with head and neck squamous cell carcinoma. *Head Neck* 2012, 34 (11), 1529-36.

What is claimed is:

1. A method for detecting head and neck cancer in a human subject, comprising
   (a) preparing genomic DNA extract comprising a genomic locus encoding a microRNA (mgmiR) from a tissue or body fluid of said human subject, said genomic DNA extract comprising a first DNA fragment encompassing at least one genomic locus encoding at least one microRNA 124-1, said tissue or body fluid being selected from the group consisting of a head tissue, a neck tissue, mouth swab, nose swab, saliva, and combination thereof,
   (b) generating a second DNA fragment by quantitative polymerase chain reaction (qPCR) using as a template said first DNA fragment and using as primers oligonucleotide pair having the sequence of SEQ ID Nos. 1 and 2,
   (c) measuring the level of said second DNA fragment generated in step (b), and
   (d) comparing the level of said second DNA fragment with a base level, said base level being the level of a corresponding DNA fragment generated by the same manner from the same tissue or body fluid of an individual known to be free from said cancer,
   wherein a significantly higher level of said second DNA fragment as compared to said base level is indicative of head and neck cancer in said human subject.

2. The method of claim 1, wherein said head and neck cancer is a head and neck squamous cell carcinoma (HN-SCC).

3. The method of claim 1, further comprising a step (d) of treating said human subject with a treatment method selected from the group consisting of surgery, chemotherapy, radiation therapy, and combination thereof.

4. The method of claim 1, wherein a 100% higher level of said second DNA fragment as compared to the base level is indicative of presence of cancer.

* * * * *